United States Patent [19]
Kaneko et al.

[11] Patent Number: 5,386,819
[45] Date of Patent: Feb. 7, 1995

[54] METHOD AND APPARATUS FOR INHIBITING A SCATTERED COMPONENT IN A LIGHT HAVING PASSED THROUGH AN EXAMINED OBJECT

[75] Inventors: Mamoru Kaneko, Hachioji; Katsuyuki Yamamoto; Koichi Shimizu, both of Sapporo, all of Japan

[73] Assignee: Olympus Optical Co., Ltd., Tokyo, Japan

[21] Appl. No.: 46,929

[22] Filed: Apr. 14, 1993

Related U.S. Application Data

[63] Continuation of Ser. No. 589,556, Sep. 28, 1990, abandoned.

[30] Foreign Application Priority Data

Mar. 29, 1990 [JP] Japan .................................. 2-81552
May 8, 1990 [JP] Japan .................................. 2-119468

[51] Int. Cl.$^6$ .............................................. A61B 1/06
[52] U.S. Cl. ........................................ 128/6; 356/341; 356/343
[58] Field of Search .................. 128/4, 6, 633, 634, 128/665; 356/39, 40, 41, 333, 338, 341, 343, 432; 250/341, 258; 378/7, 86

[56] References Cited

U.S. PATENT DOCUMENTS

| | | | |
|---|---|---|---|
| 3,662,176 | 5/1972 | Kamentsky et al. | 356/39 |
| 3,745,350 | 7/1973 | Hill et al. | 356/341 |
| 3,785,735 | 1/1974 | Friedman | 356/39 |
| 4,146,799 | 3/1979 | Pitt et al. | 356/343 |
| 4,149,080 | 4/1979 | Schittenhelm | 378/7 |
| 4,193,692 | 3/1980 | Wynn | 356/341 |
| 4,226,541 | 10/1980 | Tisue | 356/446 |
| 4,420,256 | 12/1983 | Fladda et al. | 356/341 |
| 4,595,291 | 6/1986 | Tatsuno | 356/336 |
| 4,674,879 | 6/1987 | Gregorig et al. | 356/301 |
| 4,694,833 | 9/1987 | Hamaguri | 128/633 |
| 4,807,637 | 2/1989 | Bjorkholm | 128/665 |
| 4,881,251 | 11/1989 | Nambu et al. | 378/86 |
| 4,887,285 | 12/1989 | Harding et al. | 378/86 |
| 4,898,175 | 2/1990 | Noguchi | 128/6 |
| 4,945,239 | 7/1990 | Wist et al. | 128/665 |
| 4,995,107 | 2/1991 | Klingenbeck | 378/7 |
| 5,009,230 | 4/1991 | Hutchinson | 128/633 |

OTHER PUBLICATIONS

"Road to Optical CT" of Living Body Measurement by Using Light, O plus E, published May 1987 to Mar. 1988, Series 1 to 10.

"Characterization of the Near Infrared Absorption Spectra of Cytochrome $aa_3$ and Haemoglobin for the Non-invasive Monitoring of Cerebral Oxygenation", Wray et al, Biochimica et Biophysica Acta 933, 1988, pp. 184–192.

"In vivo Transillumination of the Hand Using Near Infrared Laser Pulses and Differential Spectroscopy", Jarry et al, J. Biomed. Eng. 1989, vol. 11, Jul. 1989, pp. 293–299.

"Laser Pulse Tomography using a Streak Camera", Takiguchi et al, International Topical Meeting on Image Detection and Quality, Jul. 16–18, 1986.

*Primary Examiner*—Ralph A. Lewis
*Attorney, Agent, or Firm*—Armstrong, Westerman, Hattori, McLeland & Naughton

[57] ABSTRACT

In the method and apparatus for inhibiting a scattered component in a light having passed through the interior of an examined object, a light is radiated to the examined object, the sum of a straight advancing light component and scattered light component of the light having passed through the interior of the examined object is detected, only the scattered light component of the light having passed through the interior of the examined object is detected and the straight advancing light component is detected by an operation using the two detected outputs. In the scattered component inhibiting method and apparatus, a light modulated with a period larger than the delay of the propagating time by the scatter in the examined object is radiated to the examined object, the light having passed through the interior of the examined object is detected and the straight advancing light component is extracted by extracting a predetermined phase of the detected output. Or, in the scattered component inhibiting method and apparatus, a light of a plurality of wavelengths is radiated to the examined object, the light having passed through the interior of the examined object is detected and the scattered light component is inhibited by an operation using a plurality of detected outputs corresponding to the detected plurality of wavelengths.

10 Claims, 23 Drawing Sheets

- PARTICLE
$\mu t = \mu s + \mu a$

STANDARDIZED LIGHT INTENSITY(IN %)

STANDARDIZED LIGHT INTENSITY(IN %)

STANDARDIZED LIGHT INTENSITY(IN %)

TIME (IN ps)

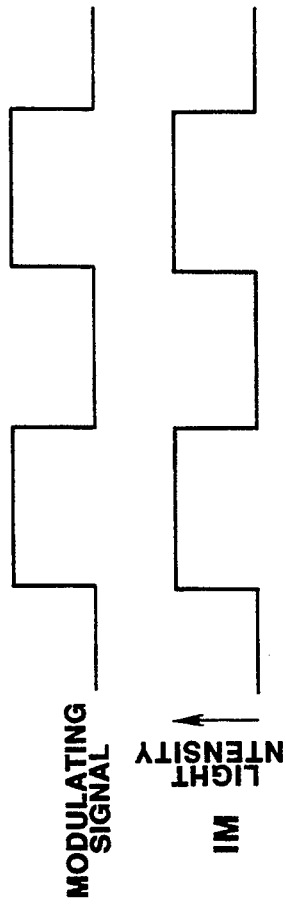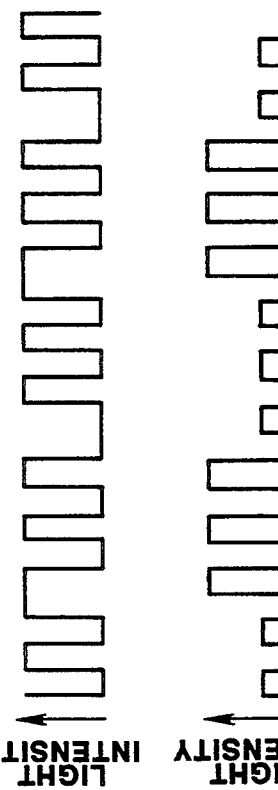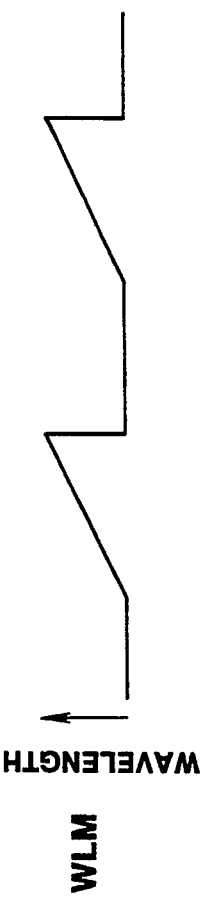
FIG.16(A) MODULATING SIGNAL
FIG.16(B) IM LIGHT INTENSITY
FIG.16(C) FM/IM LIGHT INTENSITY
FIG.16(D) PM/IM LIGHT INTENSITY
FIG.16(E) AM/IM LIGHT INTENSITY
FIG.16(F) WLM WAVELENGTH

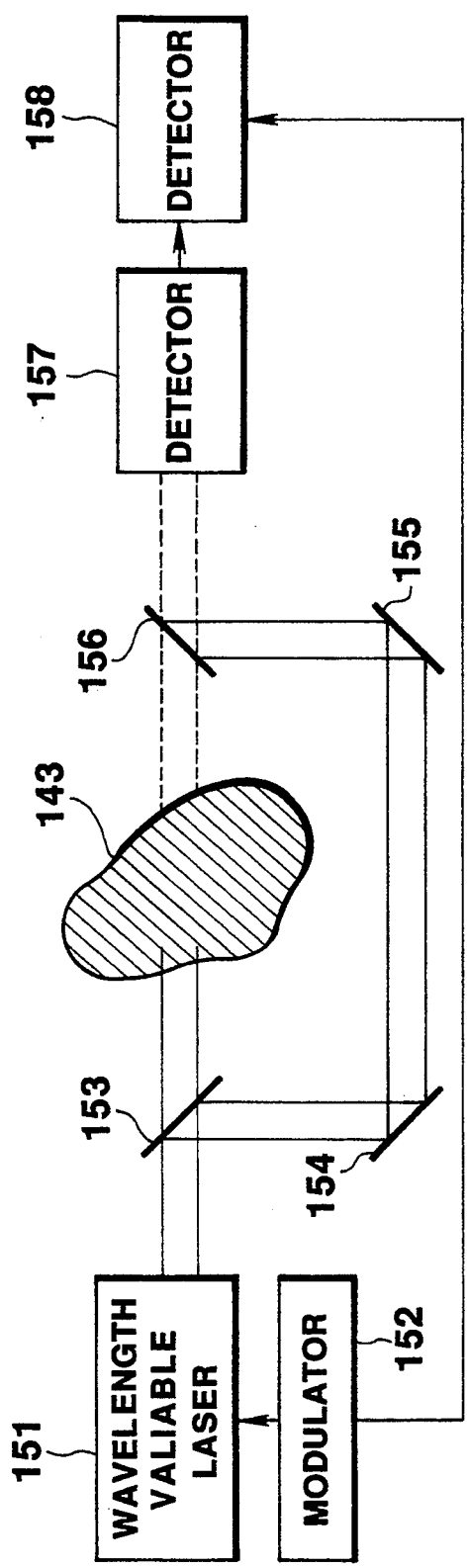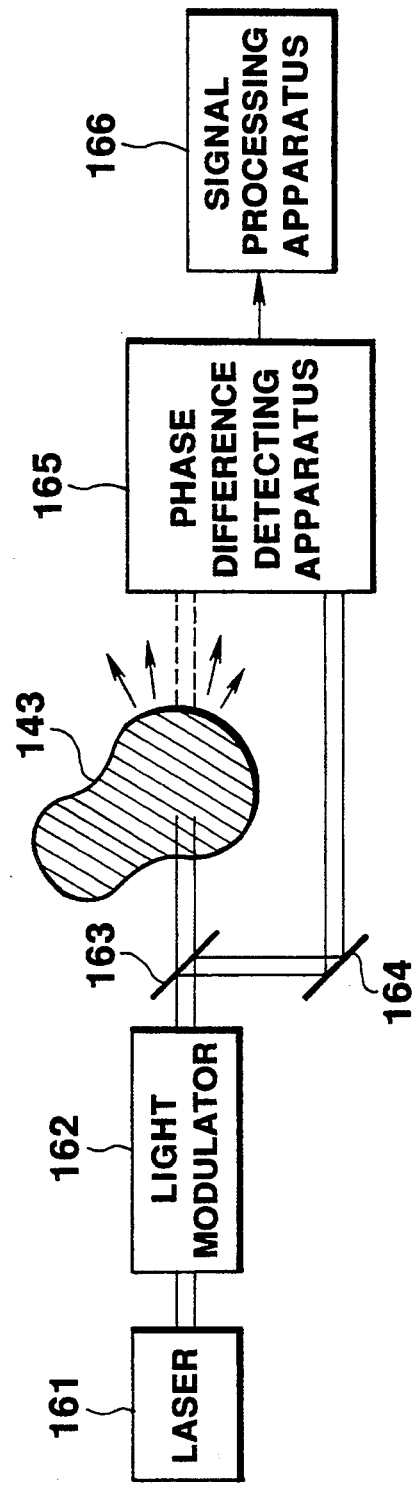

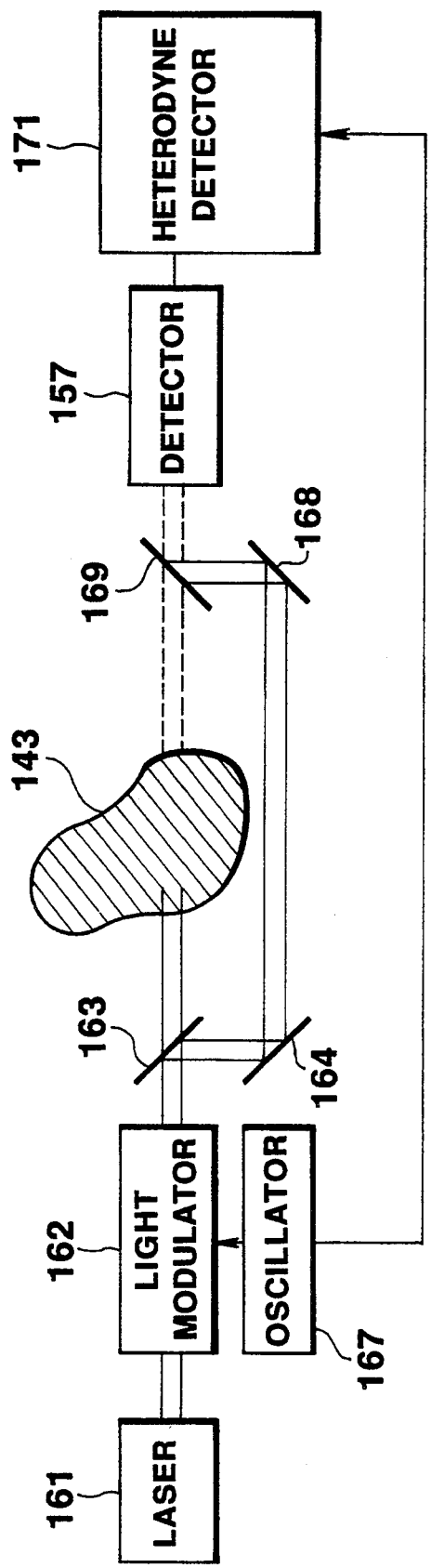
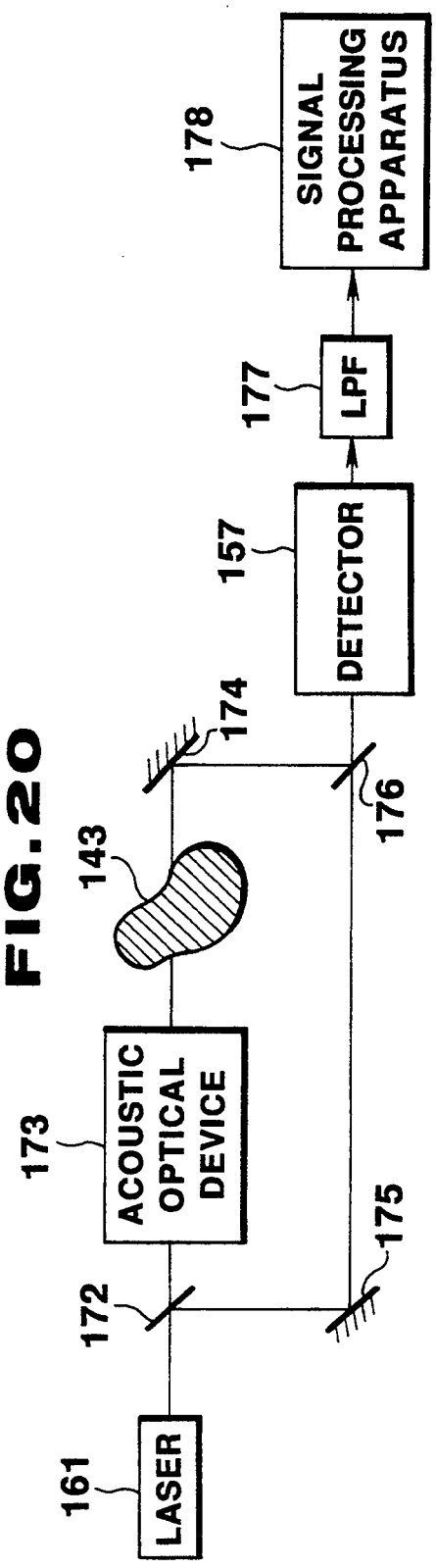

FIG. 31
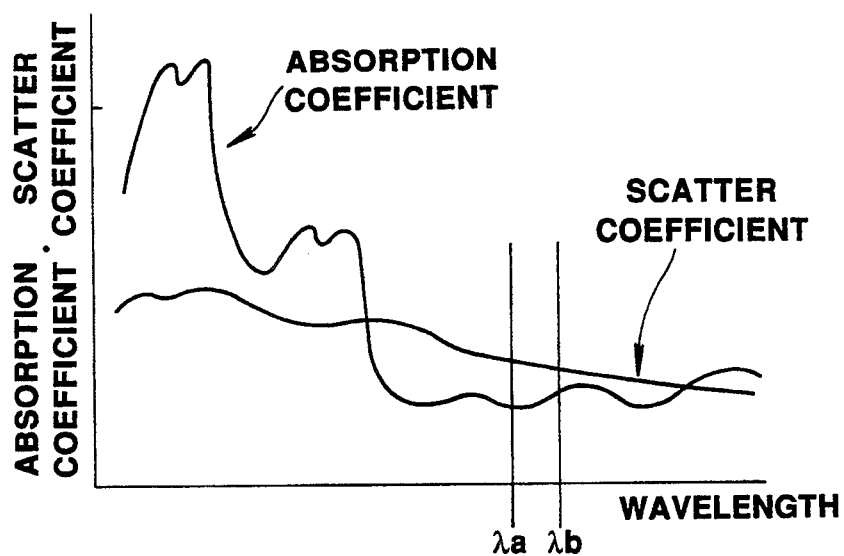
FIG. 32(A) $\lambda_1$ 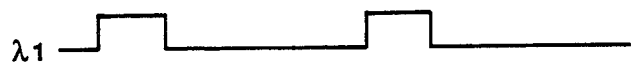
FIG. 32(B) $\lambda_2$ 
FIG. 32(C) $\lambda_3$ 
FIG. 32(D) $\lambda_4$ 
FIG. 33(A) $\lambda_1$ 
FIG. 33(B) $\lambda_2$ 
FIG. 33(C) $\lambda_3$ 
FIG. 33(D) $\lambda_4$ 

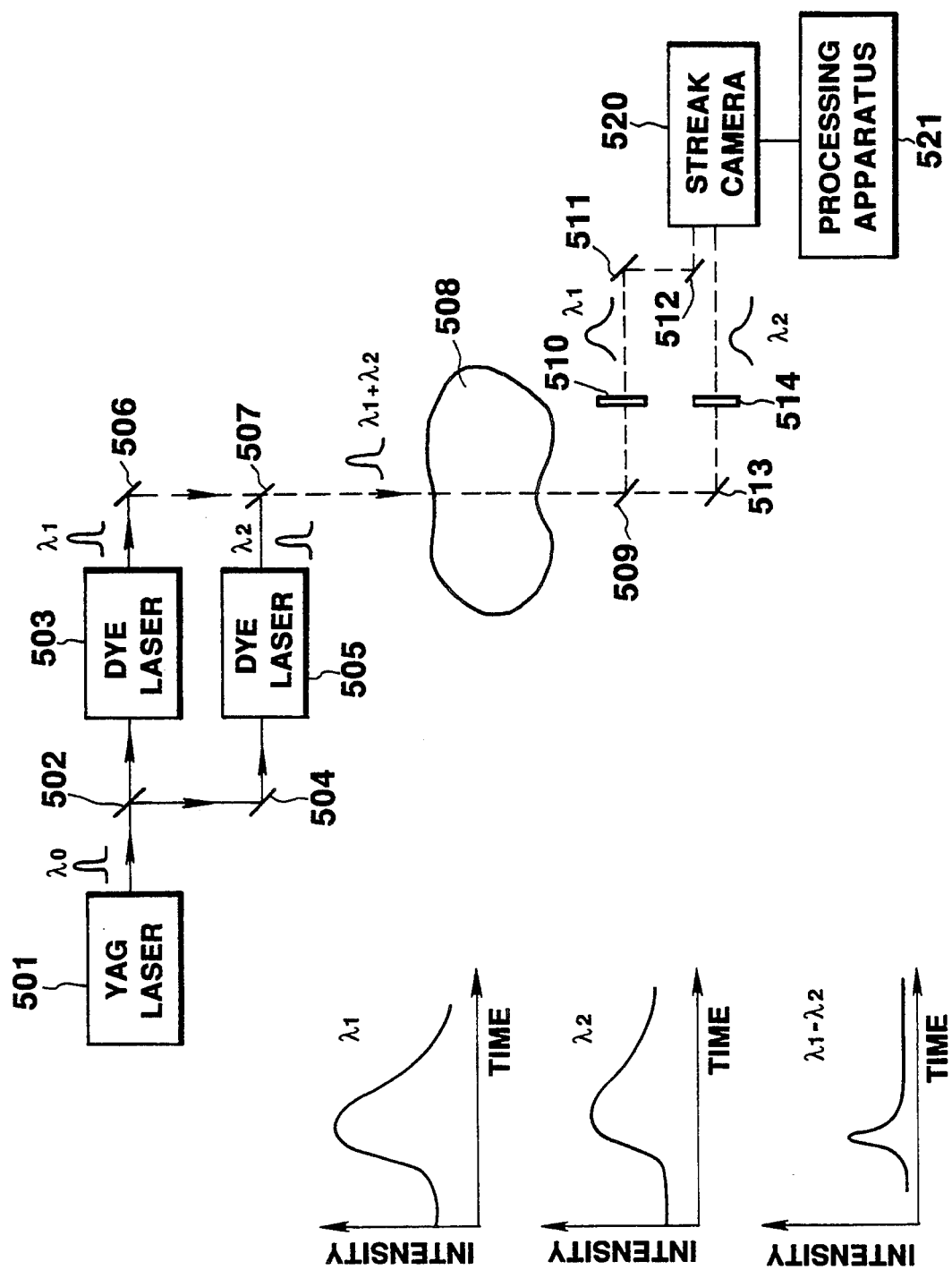

METHOD AND APPARATUS FOR INHIBITING A SCATTERED COMPONENT IN A LIGHT HAVING PASSED THROUGH AN EXAMINED OBJECT

This application is a continuation of application Ser. No. 07/589,556 filed Sep. 28, 1990, now abandoned.

BACKGROUND OF THE INVENTION

1. Field of the Invention

This invention relates to a method and apparatus for inhibiting a scattered component in a light having passed through an examined object adapted to make the information within the inspected object visible by using a light in order to help the perspective of a living body by a light, the cross-sectioned image photographing of a living body by a light, the non-destructive inspection of the internal structure of a semiconductor or IC or the work in mist, snow or water.

2. Related Art Statement

Recently, with the increase of the diseases of the heart circulatory system and brain vein system and with the prevalence of the image utilization in the diagnosis, the importance of vein imaging has increased. However, although vein imaging has become comparatively easy due to the progress of digital radiography, the danger and pain experienced by the examinee when vein imaging is applied to a human body must be considered.

Heretofore, the non-invading or non-contacting measurement of the information within such examined object as a living body has been made mostly by x-rays. However, the use of x-rays is known to cause radiation of radioactive rays and their use is poorly adapted for imaging a living body function. Also, the NMR-CT method has the problem that the apparatus is large and expensive. The perspective obtained by ultrasonic waves suffers from low spatial analyzing activity. Heretofore, it has been considered that the living body or IC substrate is non-transparent and the interior can not be viewed by using a light.

It is well known that blood hemoglobin (Hb) shows a peculiar spectral variation in response to the oxygenizing degree against the light in the near infrared region. By utilizing this feature, as shown, for example, in the article "Living Body Measurement by Using Light" found in the magazine "O plus E" May 1987 to March 1988, research relating to such non-invading measurement of the information within a living body, such as the measurement of the oxygen saturation degree of blood, are being actively made. The blood hemoglobin (Hb) absorbs so much more light in the infrared region than living body tissue that the possibility of detecting a light image of a vein in the tissue is considered feasible.

However, where the living body interior is observed from outside the body by using a light, because of strong light scattering of the tissue within or without the body, the contrast will be reduced and it will be difficult to make the information of the interior of a living body visible. It is expected that, if the problem of this light scattering can be solved, the shape and variation of a vein within the body will be able to be made visible with an actual time and to be measured. It is expected that, from the thus obtained body interior information, on the basis of a knowledge of spectral science, the information of not only the shape but also the metabolic function of the living body can be obtained.

OBJECT AND SUMMARY OF THE INVENTION

An object of the present invention is to provide a method and apparatus for inhibiting a scattered component of a light passing through an examined object, in order to inhibit the influence of the scattering on the examined object so that the information within the examined object may be made visible by using a high resolution light.

In a preferred method and apparatus for inhibiting a scattered component in a light passing through an examined object of the present invention, a light is radiated to the examined object, and the sum of a straight advancing light component and a scattered light component of the light having passed through the interior of the examined object is detected. Then, only the scattered light component of the light having passed through the interior of the examined object is detected, and the straight advancing light component is extracted by an operation using the two detected outputs.

In another embodiment of the scattered component inhibiting method and apparatus, the light modulated by a period larger than the delay of the propagating time by the scattering in the examined object of the light passing through the interior of the examined object is radiated to the examined object. Then, the light having passed through the interior of the examined object is detected and the straight advancing light component is extracted by extracting a predetermined phase component of the detected output.

In still another embodiment the scattered component inhibiting method and apparatus, a light of a plurality of wavelengths is radiated to the examined object. Then, the light having passed through the interior of the examined object is detected and the scattered light component is inhibited by an operation using a plurality of detected outputs corresponding to the detected plurality of wavelengths.

The other features and advantages of the present invention will become apparent enough with the following explanation.

BRIEF DESCRIPTION OF THE DRAWINGS

FIG. 1 is an explanatory view showing the formation of an apparatus for realizing a scattered component inhibiting method.

FIG. 2 is a characteristic diagram showing a measured result of a transmitted light amount near an edge on which the apparatus of FIG. 1 is used.

3

Figure 8:
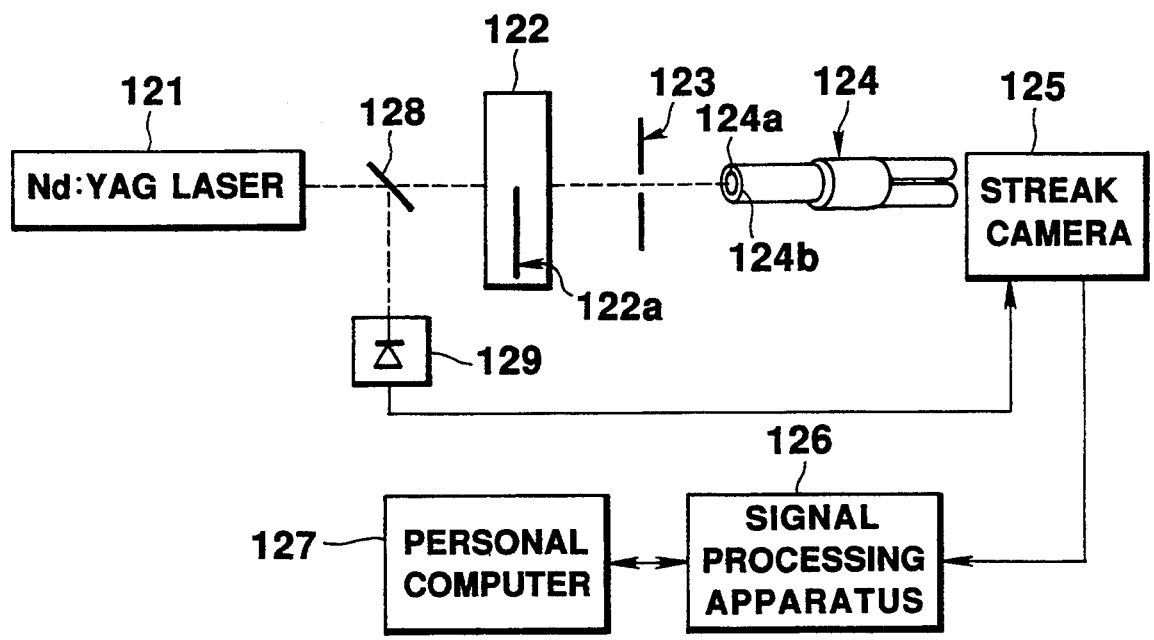
FIG. 8 is an explanatory diagram showing the formation of an apparatus for realizing a scattered component inhibiting method.
Figure 9:
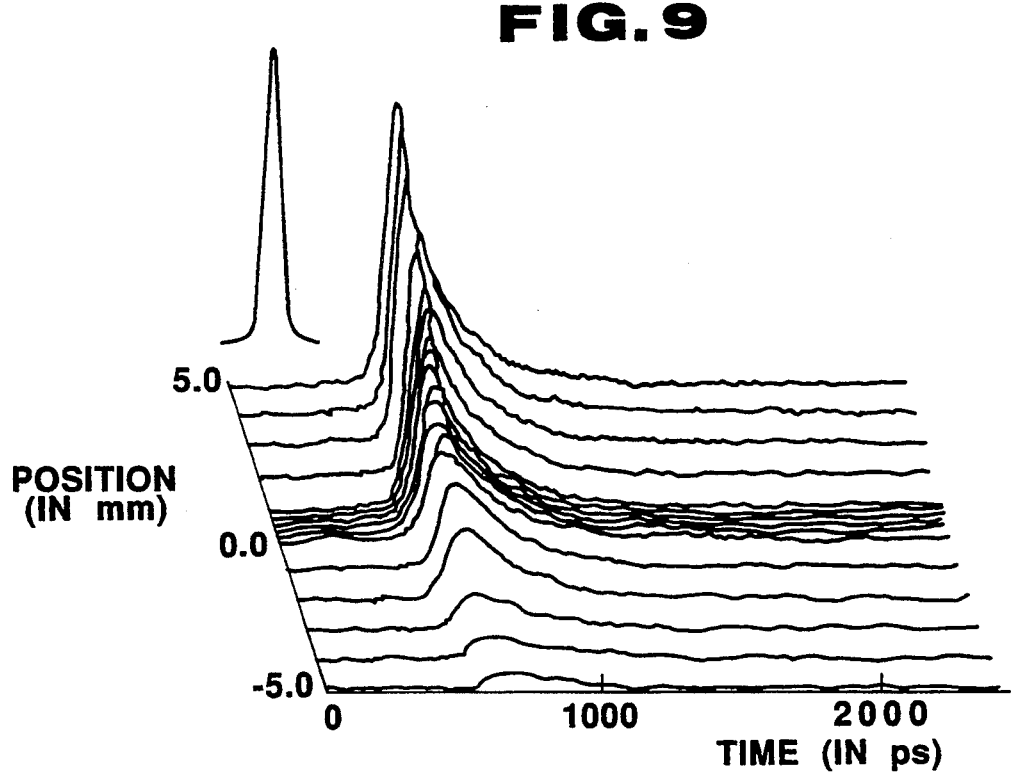

FIG. 9 is a waveform diagram showing time analyzed waveforms detected in a fiber center part in the apparatus of FIG. 8.

Figure 10:
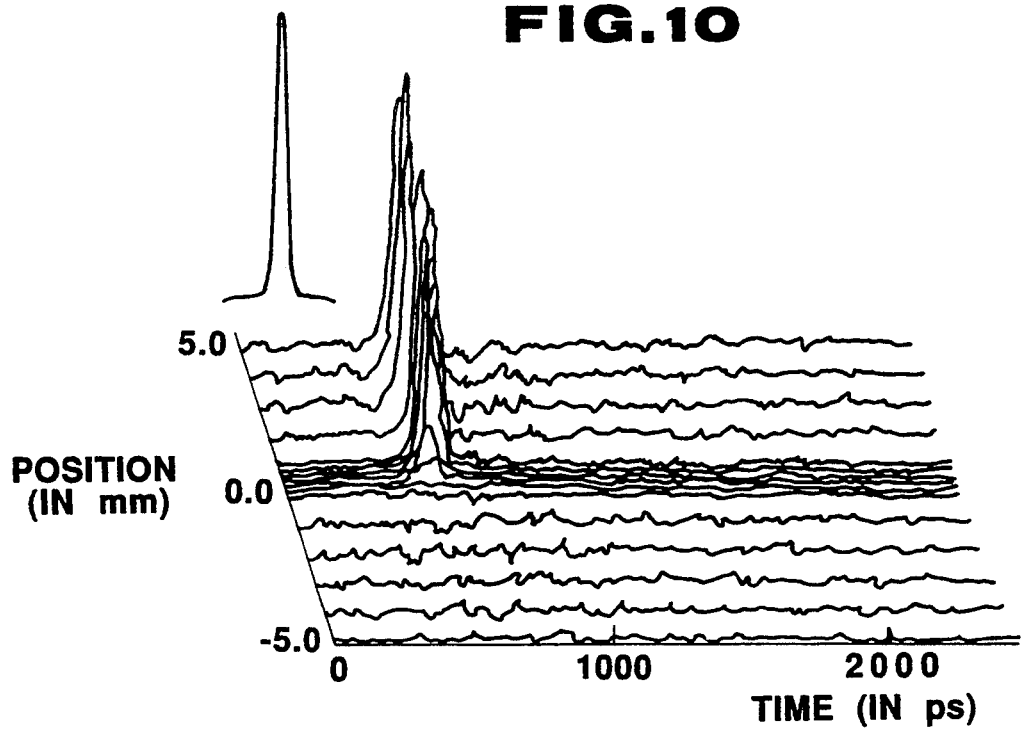

FIG. 10 is a waveform diagram showing the differences between the time analyzed waveforms detected in the fiber center part in the apparatus of FIG. 8 and the time analyzed waveforms detected in the fiber peripheral part.

Figure 11:
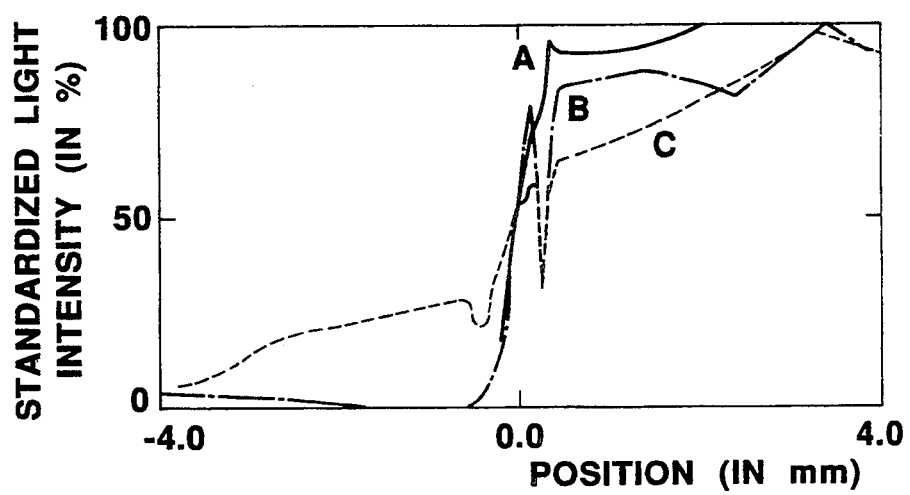

FIG. 11 is a characteristic diagram showing measured results of transmitted light amounts near an edge on which the apparatus of FIG. 8 is used.

Figure 12:
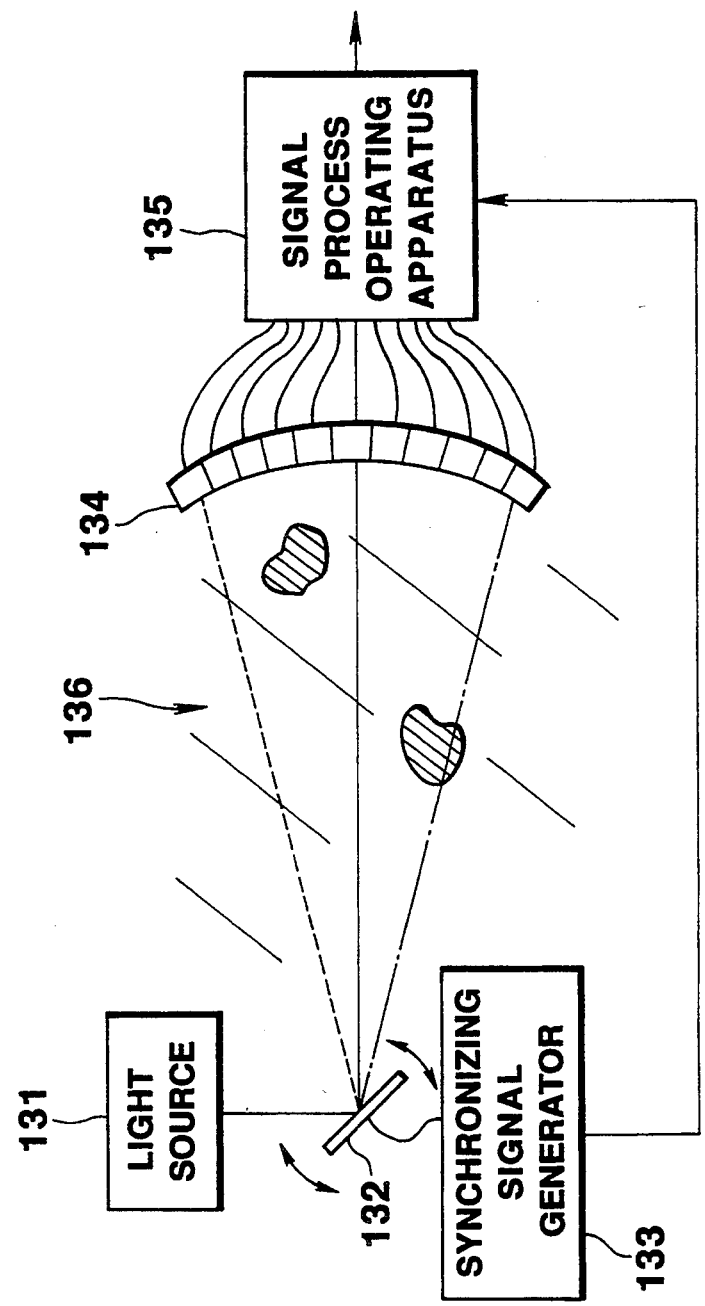

FIG. 12 is an explanatory diagram showing the schematic formation of a perspective apparatus making a perspective in a wide range possible.

FIGS. 13 to 20 relate to the third embodiment of the present invention.

Figure 13:
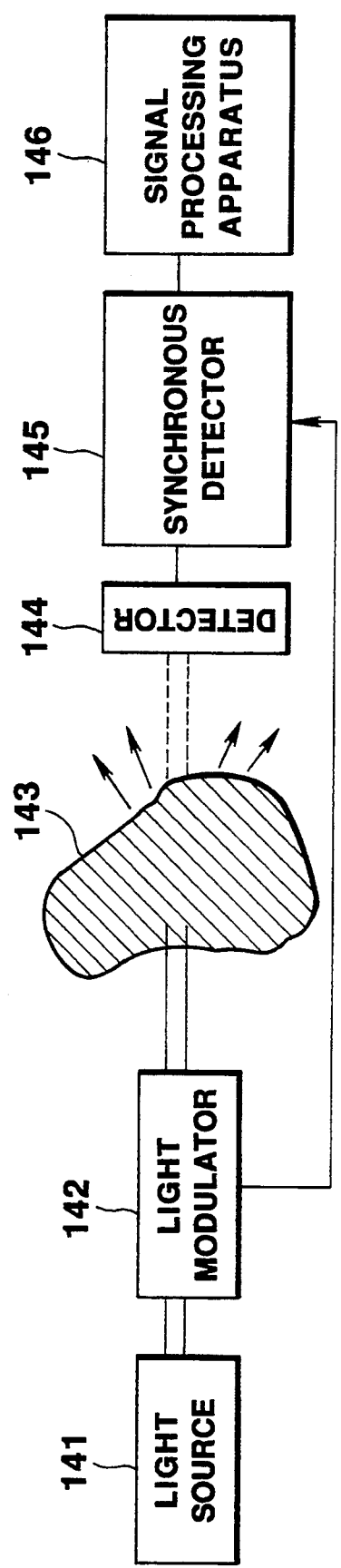

FIG. 13 is an explanatory diagram showing the schematic formation of an apparatus for realizing a scattered component inhibiting method.

Figure 14:
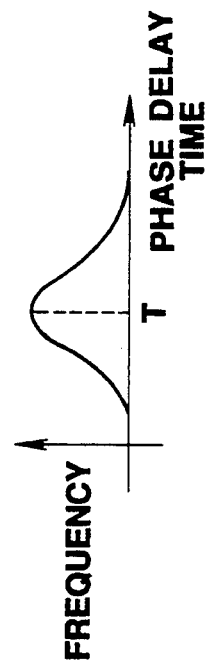

FIG. 14 is a histogram showing the distribution of time delays by the scattering.

Figure 15A:
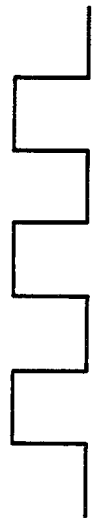
Figure 15B:
Figure 15C:

FIGS. 15(A) to (C) are respectively waveform diagrams for explaining the operation of the apparatus of FIG. 13.

FIGS. 16(A) to (F) are waveform diagrams showing modulated incident lights.

FIG. 17 is an explanatory view showing the schematic formation of a scattered component inhibiting apparatus utilizing wavelength modulation.

FIG. 18 is an explanatory view showing the schematic formation of a scattered component inhibiting apparatus utilizing a reference light for inhibiting the scattered component.

FIGS. 19 and 20 are explanatory views showing respectively the concrete formation examples of the apparatus of FIG. 18.

FIGS. 21 to 36 relate to the fourth embodiment of the present invention.

Figure 21:
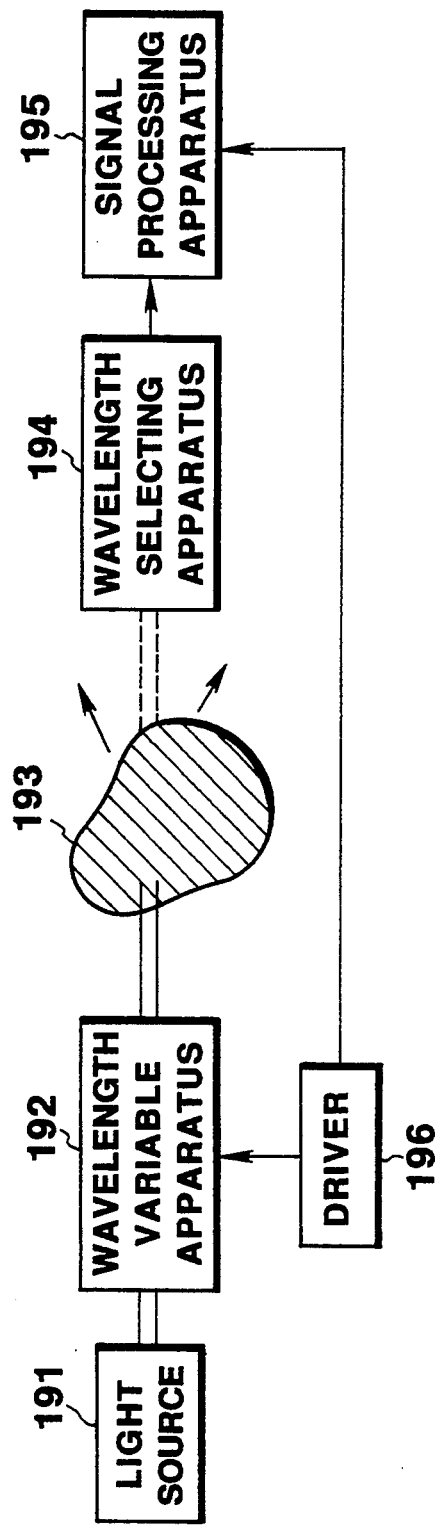

FIG. 21 is an explanatory view showing the schematic formation of an apparatus for realizing a scattered component inhibiting method.

Figure 23:
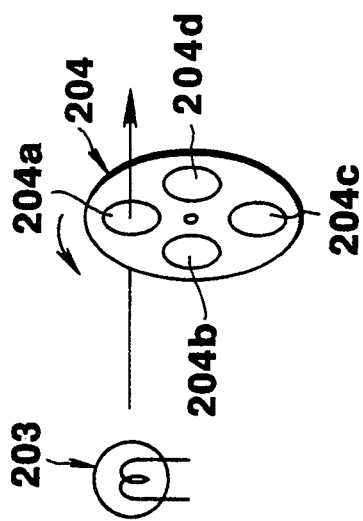
Figure 22:
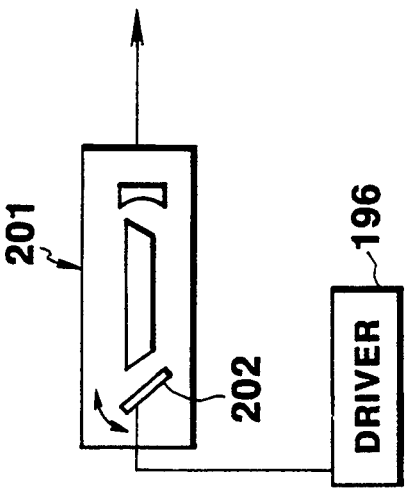
Figure 24:
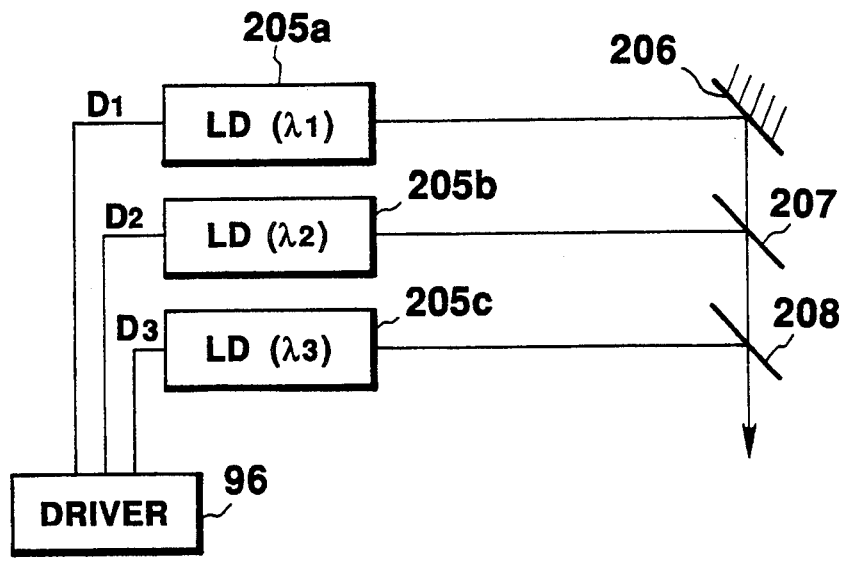
Figure 25A:
Figure 25B:
Figure 25C:
Figure 25D:
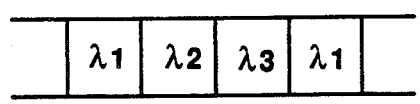

FIGS. 22 to 24 are explanatory views respectively showing the examples of a light source and wavelength variable apparatus.

FIGS. 25(A) to (D) are respectively timing charts for explaining the operations of the apparatus of FIG. 24.

Figure 26:
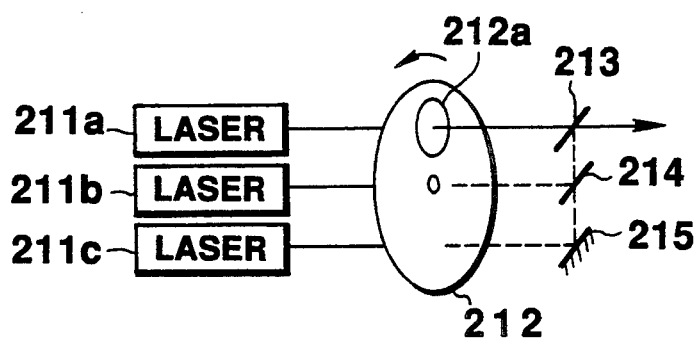

FIG. 26 is an explanatory view showing examples of a light source and wavelength variable apparatus.

FIGS. 27 to 30 are explanatory views respectively showing examples of a wavelength selecting apparatus.

FIG. 31 is a characteristic diagram showing the wavelength characteristics of an absorption coefficient and scatter coefficient.

FIGS. 32(A) to (D) are timing charts respectively showing the exit timings of respective wavelengths.

FIGS. 33(A) to (D) are waveform diagrams respectively showing the waveforms of the lights of respective wavelengths after passing through the examined object.

Figure 34:
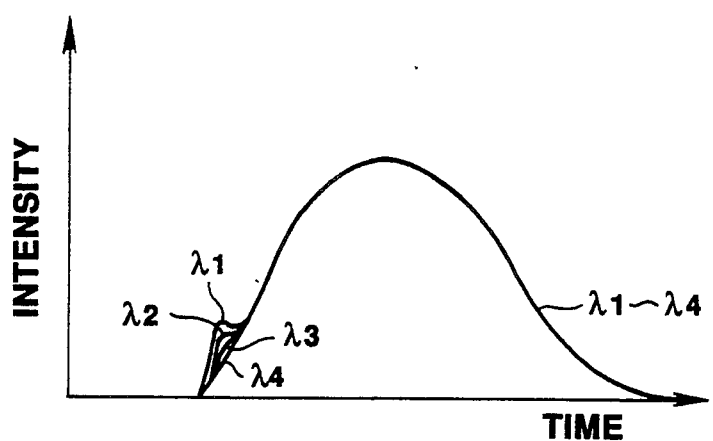

FIG. 34 is a characteristic diagram showing the relation between the intensity of the lights of respective wavelengths and the time.

Figure 4:
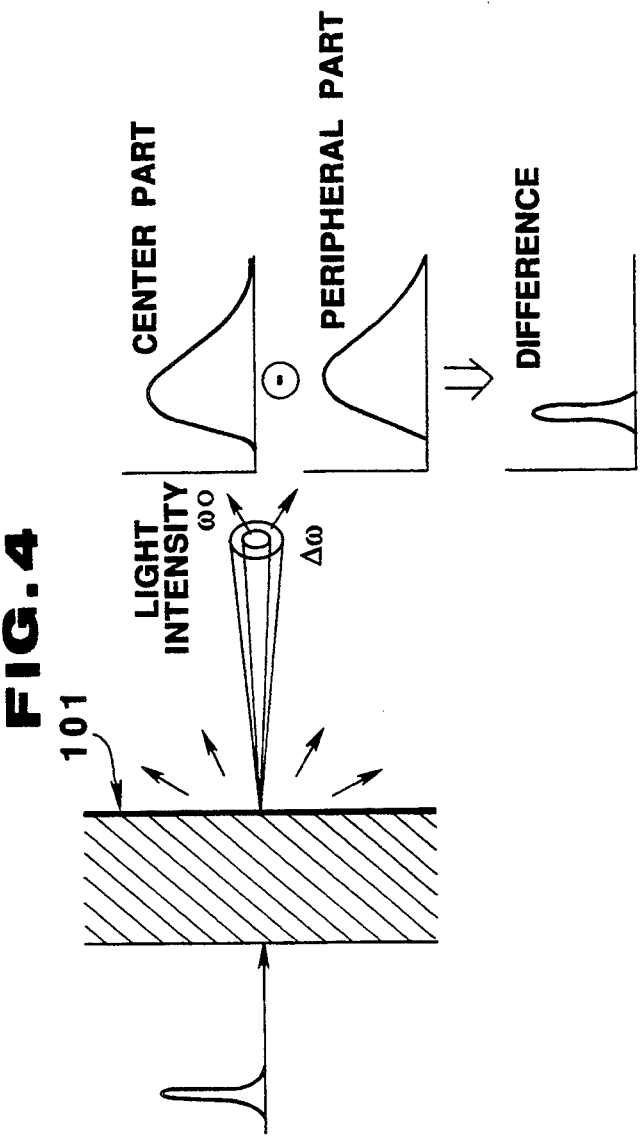
FIG. 4 is an explanatory view for explaining the principle of a scattered component inhibiting method.
Figure 35:
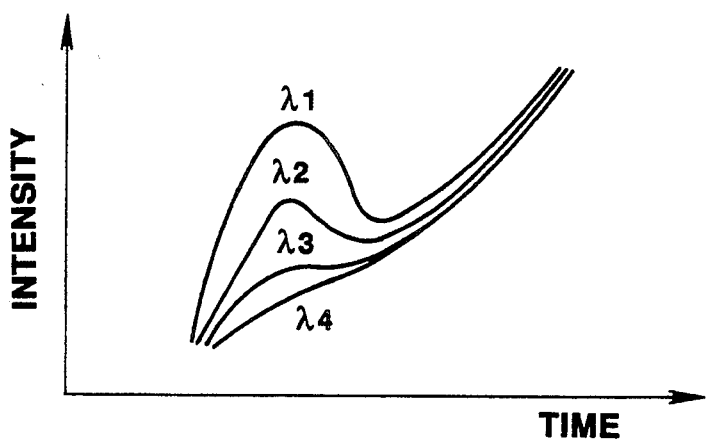

FIG. 35 is a magnified diagram of the essential part of FIG. 4.

Figure 36:
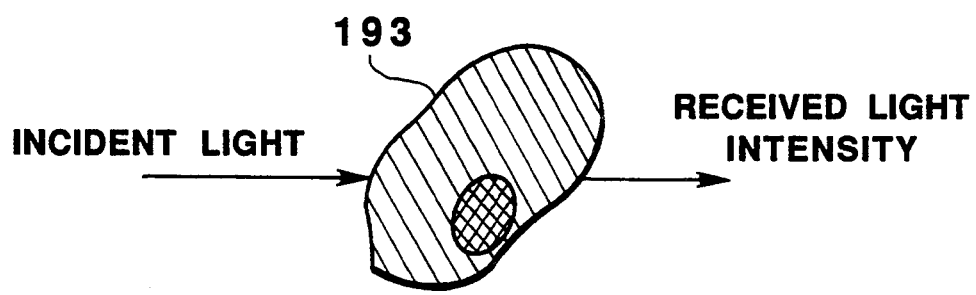

FIG. 36 is an explanatory view for explaining the relation between the intensity of the light having passed through the examined object and the examined object.

Figure 37:
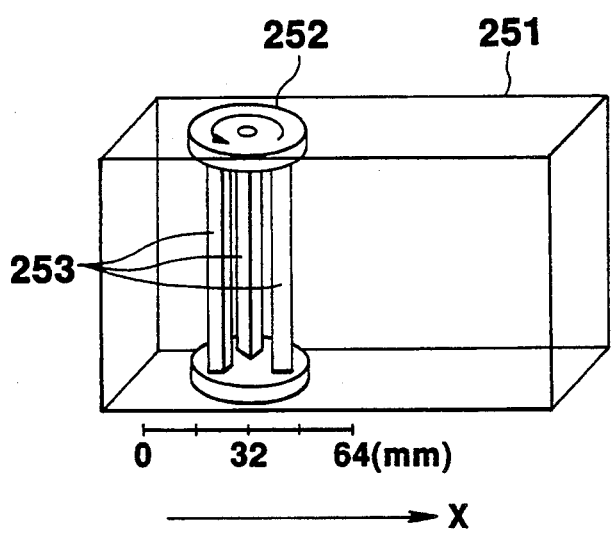

FIG. 37 is a perspective view of a living body model.

Figure 38:
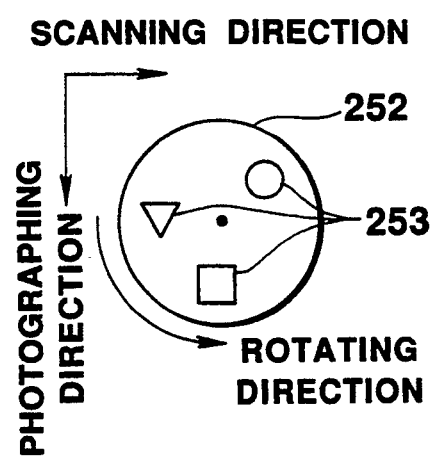

FIG. 38 is a plan view of the essential part of FIG. 37.

Figure 39:
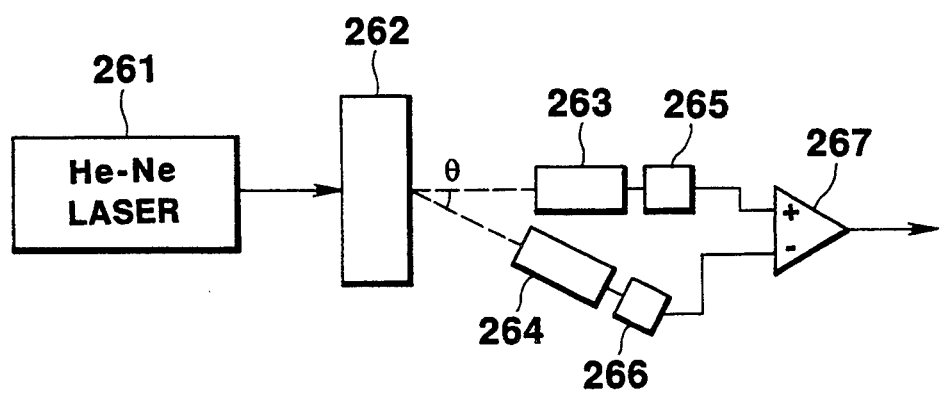
Figure 40A:
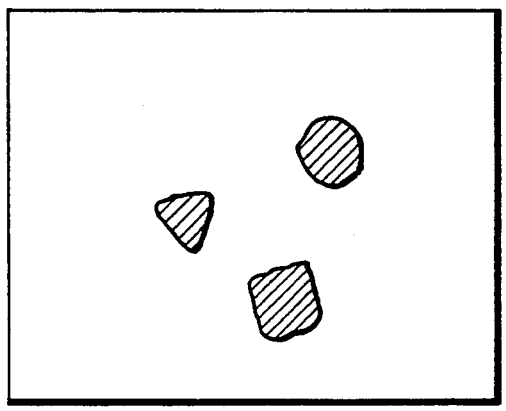
Figure 40B:
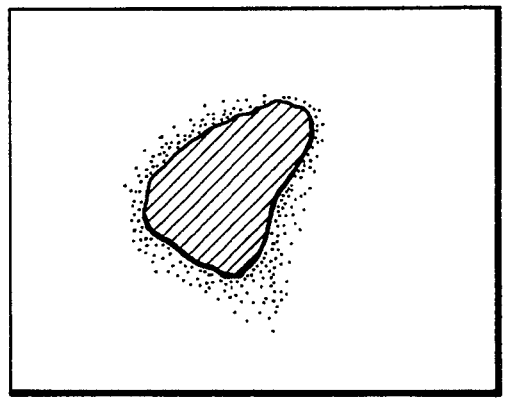
Figure 40C:
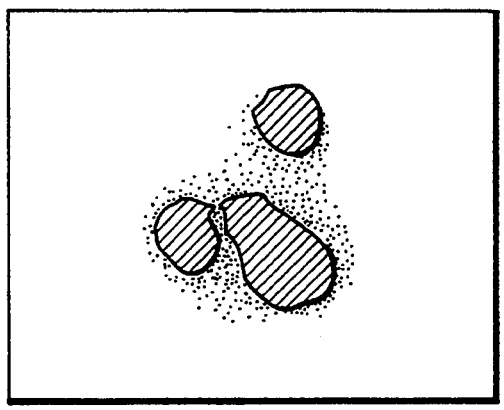
Figure 40D:
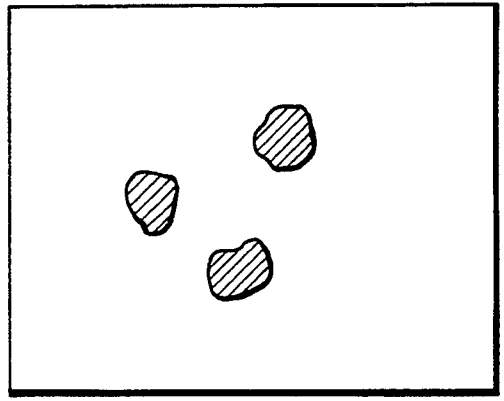

FIG. 39 is an explanatory view for explaining the principle of the difference method.

FIGS. 40 (A) to (D) are respectively explanatory views showing experimental results.

Figure 41:
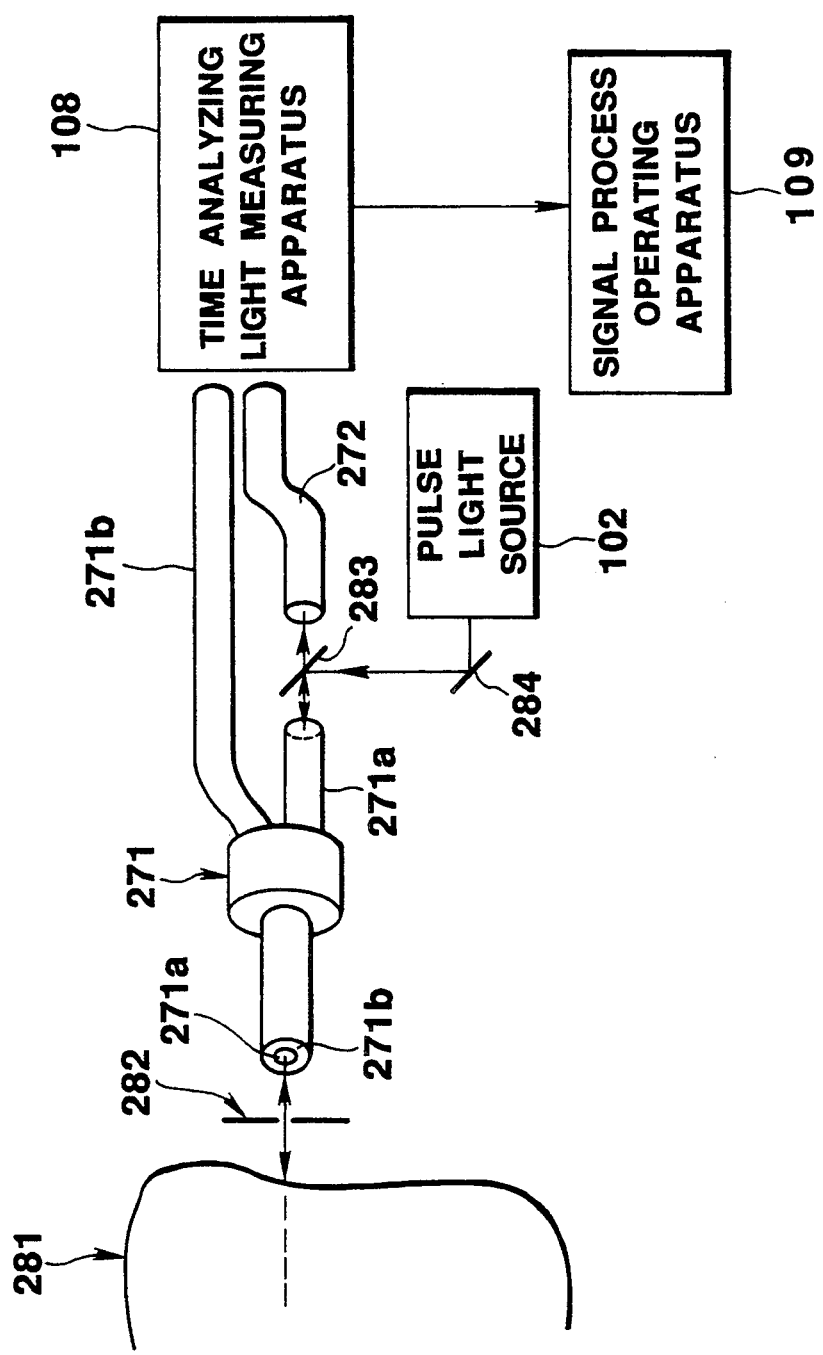

FIG. 41 is an explanatory view showing a scattered component inhibiting system of the fifth embodiment of the present invention.

Figure 42:
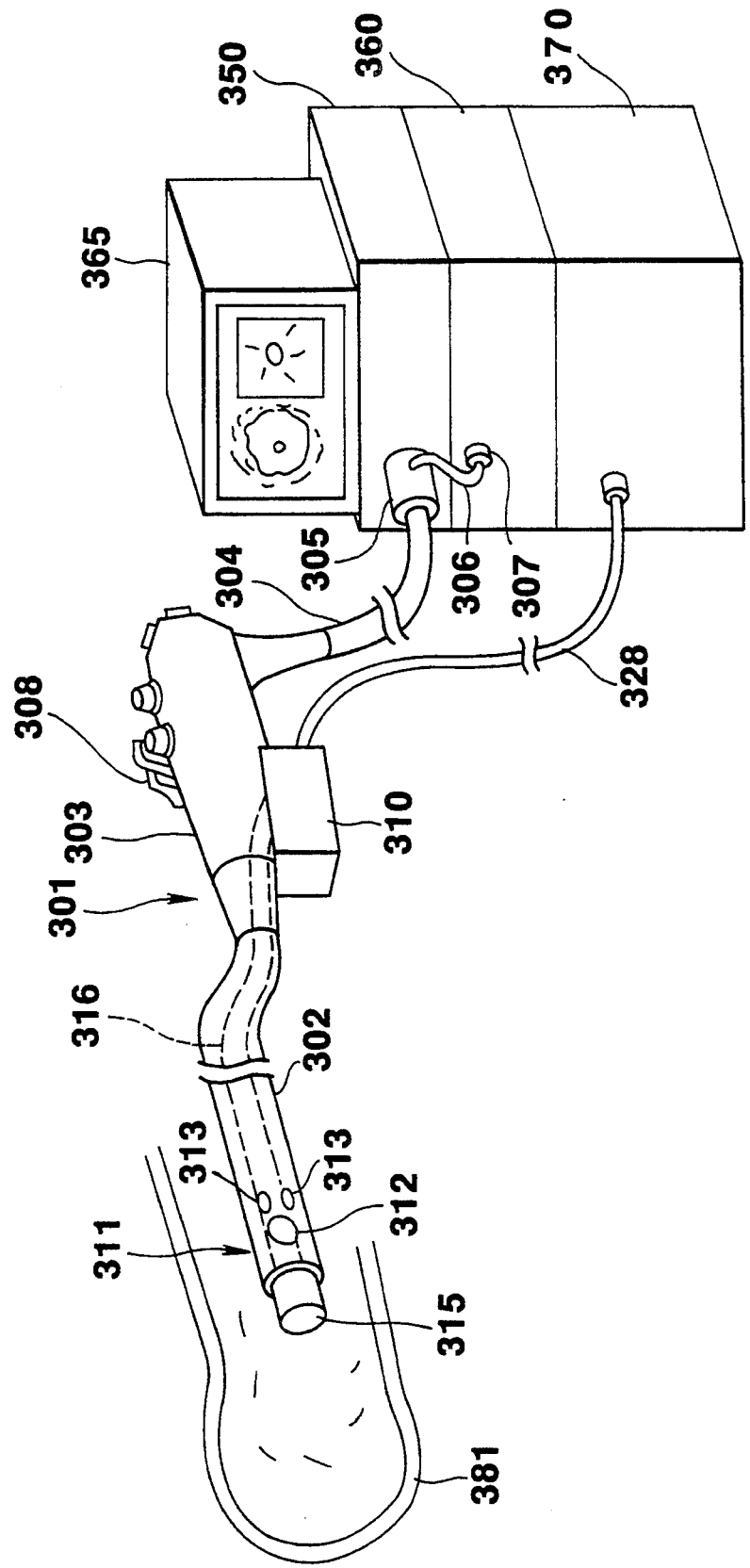
Figure 43:
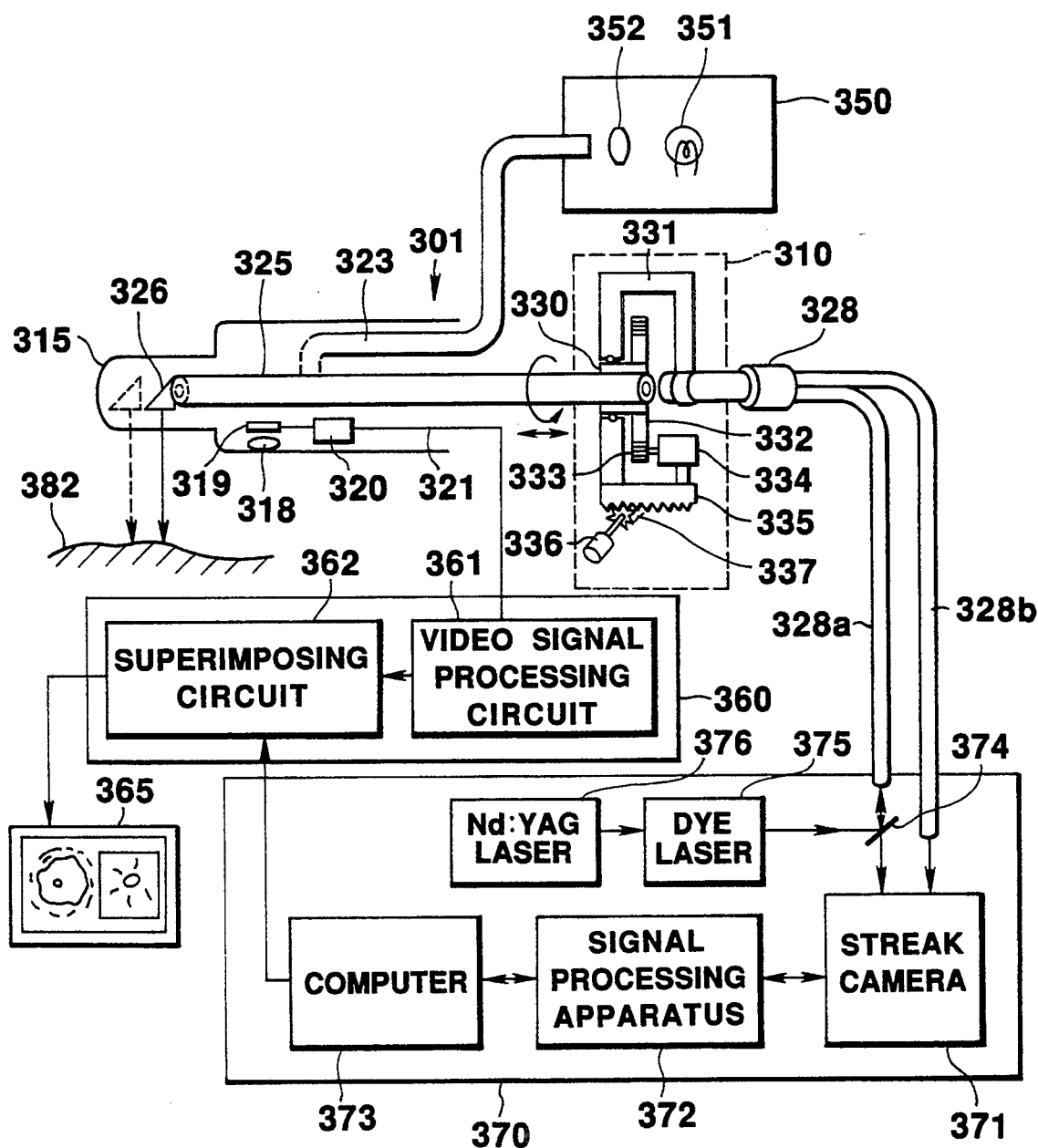

FIGS. 42 and 43 relate to the sixth embodiment of the present invention.

FIG. 42 is an explanatory view showing the whole of an endoscope system.

FIG. 43 is an explanatory view showing the formation of the endoscope system.

Figure 44:
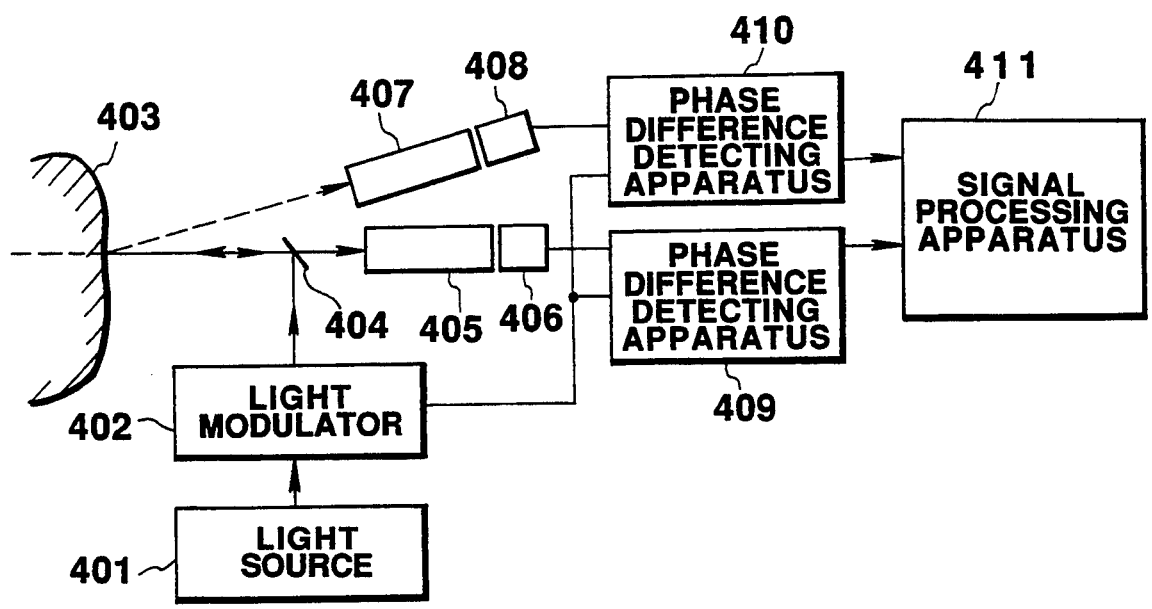

FIGS. 44 and 45 relate to the seventh embodiment of the present invention.

FIG. 44 is an explanatory view showing a scattered component inhibiting system.

Figure 45A:
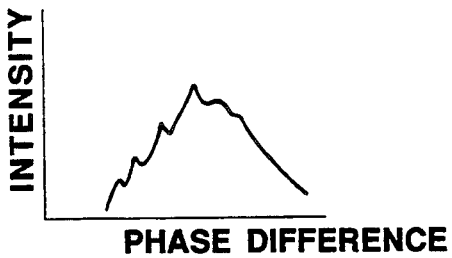
Figure 45B:
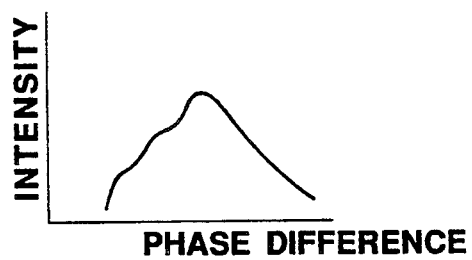
Figure 45C:

FIGS. 45(A) to (C) are characteristic diagrams for explaining the operation of this embodiment.

FIGS. 46 and 47 relate to the eighth embodiment of the present invention.

FIG. 46 is an explanatory view showing a scattered component inhibiting system.

FIGS. 47(A) to (C) are characteristic diagrams for explaining the operation of this embodiment.

DETAILED DESCRIPTION OF THE PREFERRED EMBODIMENTS

Figure 1:
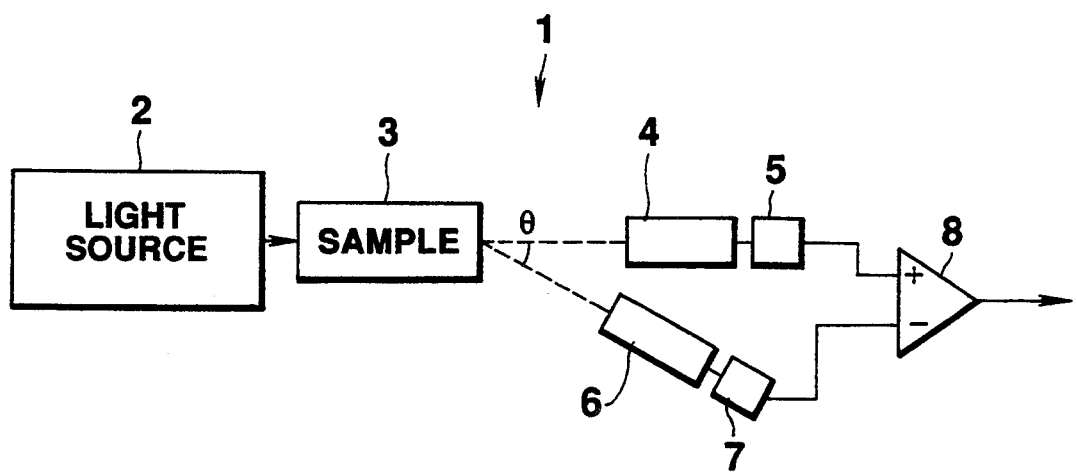
FIGS. 1 and 2 relate to the first embodiment of the present invention.
Figure 2:
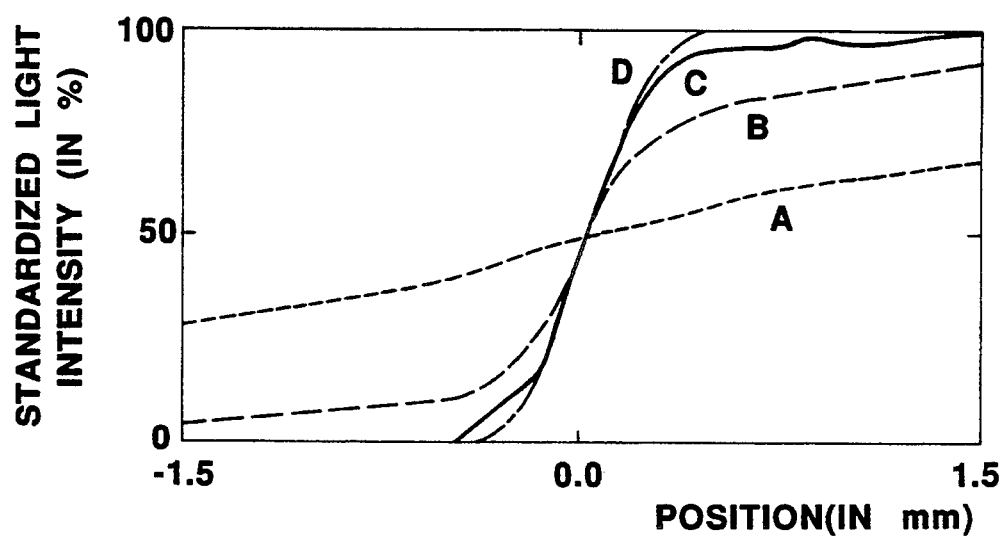

FIGS. 1 and 2 show a first embodiment of the present invention.

As shown in FIG. 1, a scattered component inhibiting apparatus 1 for realizing the scattered component inhibiting method of this embodiment comprises a light source 2 as a light radiating means and first and second light detectors 5 and 7 opposed to said light source 2 with a sample 3 held between. A first collimator 4 correctly aligned with the optical axis of the beam light from said light source 2 is connected to said first light detector 5 on the light receiving side so that the sum of the straight advancing light component emitted from said light source 2 and having passed through the sample 3, and the scattered light component may be detected by this first light detector 5. On the other hand, a second collimator 6 arranged at a fixed angle $\theta$ with said beam light is connected to the second light detector 7 so that only the scattered light component emitted from the light source 2 and having passed through the sample 3 may be detected by this second light detector 7. The respective outputs of the first and second light detectors 5 and 7 are input into a differential amplifier 8. When the output of the second light detector 7 weighted by $\theta$ is subtracted from the output of the first light detector 5 by this differential amplifier 8, the scattered light component will be greatly reduced. This shall be provisionally called a differential principle.

An experiment for showing the effect of this embodiment shall be explained in the following with reference to FIG. 2.

In this experiment, an He—Ne laser (of a wavelength of 632.8 nm and an output of 2 mW) was used for the light source 2, a combination of an objective lens (of a focal distance of 10 mm) and pinhole (of a diameter of 30 $\mu$m) was used for the first collimator 4 and a beam expander (of $\times 10$) was used for the second collimator 6. A milk ball suspension contained in a container made of acrylic having an inside wall thickness of 20 mm as a scattering substance was used for the sample 3. A knife edge was arranged in the central part within this solution and the transmitted light amount near the edge was measured.

The results are shown in FIG. 2 in which the abscissa represents the position of the beam center with respect to the knife edge and the ordinate represents the standardized light intensity. A shows the case of the output of the first light detector not using first collimator 4, B shows the case of the output of the first light detector 5 using the collimator 4, C shows the case by the differential principle, that is the case of the output of the differential amplifier in which the output of the second light detector 7 weighted by $\theta$ was subtracted from the output of the first light detector 5 using the first collimator 4 and D shows the case of only water having no scatter.

As seen from this FIG. 2, in the case (A) using no collimator, a strong influence of a scattered light was received and the smoothing of the signal was more remarkable than in the case (D) of only water. On the other hand, the scattered component was inhibited to some extent even by the use (B) of only the collimator and further, in the case (C) by the differential principle, a result very close to the state (D) of water having no scatter was obtained.

Thus, according to this embodiment, the straight advancing component can be extracted by inhibiting the scattered component so that even a substance which is known to strongly scatter light, having been so far thought to be unable to be perspectively viewed, may have a perspective image high in the spatial resolution measured.

FIGS. 3 to 12 show the second embodiment of the present invention.

First of all, the principle of the scattered component inhibiting method of this embodiment shall be explained with reference to FIGS. 3 to 7.

As shown in FIG. 4, when a beam-like pulse light is radiated to a scattering object 101, the light pulse will expand in the space-time direction. Therefore, the respective lights within a fine solid angle $\omega_o$ on the optical axis and within the same solid angle $\Delta\omega$ outside the axis are detected and the respective time analyzed waveforms for them are determined. Here, when the light reaching the fine solid angle $\omega_o$ (mentioned as a center part in FIG. 4) including the optical axis is detected, the sum of the straight advancing component and the scattered component will be detected. When the light reaching the solid angle $\Delta\omega$ (mentioned as a peripheral part in FIG. 4) is detected, only the scattered component will be detected. When the difference of the light intensity is taken for the respective times of these two time analyzed waveforms, as shown in the lowermost part on the left side of FIG. 4, the scattered component will be inhibited with respect to the time and space and the straight advancing component will be able to be extracted.

Figure 3:
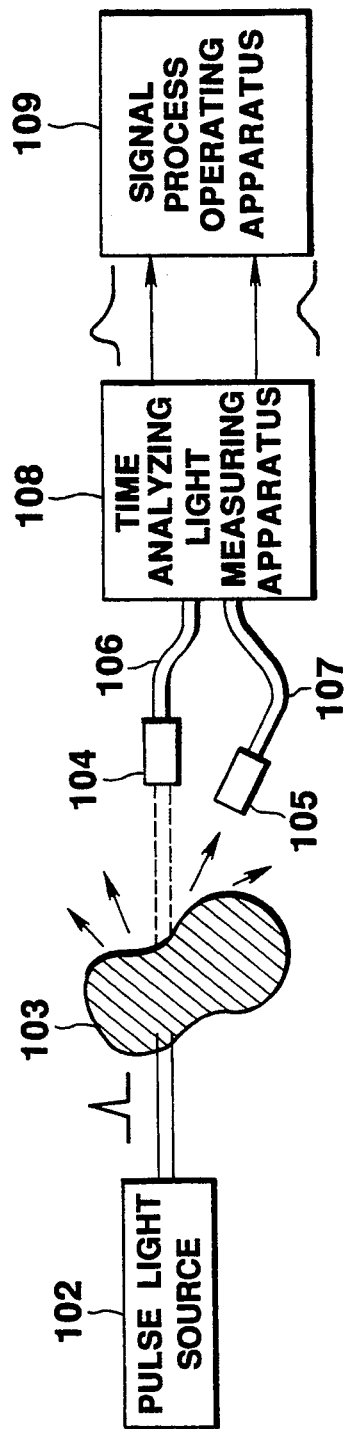
FIG. 3 is an explanatory view showing a schematic formation of an apparatus for realizing a scattered component inhibiting method.

Therefore, as shown, for example, in FIG. 3, the apparatus realizing the above principle comprises a light source 102 emitting a pulse of light, a first collimator 104 opposed to the light source 102 by holding a sample 103 between and arranged on the optical axis of the emitted light of the light source 102, a second collimator 105 opposed to the light source 102 by holding the sample 103 between and arranged outside the optical axis of the emitted light of the light source 102, optical fibers 106 and 107 connected respectively at one end to the respective collimators 104 and 105, a time analyzing light measuring apparatus 108 to which said optical fibers 106 and 107 are connected at the other ends and a signal processing operating apparatus 109 for making a predetermined operation by using the output signal of this time analyzing light measuring apparatus 108.

In the apparatus shown in FIG. 3, the pulse light emitted from the pulse light source 102 is radiated to the sample 103, the sum of the straight advancing component and scattered component having passed through this sample 13 is received by the collimator 104 and is detected by the time analyzing light measuring apparatus 108 through the optical fiber 106. Only the scattered component of the light having passed through the sample 103 is received by the collimator 105 and is detected by the time analyzing light measuring apparatus 108 through the optical fiber 107. In the time analyzing light measuring apparatus 108, the time analyzed waveform of the sum of the straight advancing component and scattered component and the time analyzed waveform of only the scattered component are detected and are fed to the signal processing operating apparatus 109. The rising part of the time analyzed waveform of the sum of the straight advancing component and scattered component corresponds to the straight advancing component propagated through the shortest light path. In the signal processing operating apparatus 109, the difference between said two time analyzed waveforms is obtained. The obtained difference is substantially the rising part of the time analyzed waveform of the sum of the straight advancing component and scattered component, and the straight advancing component is extracted by detecting this difference.

The result of a computer simulation by the Monte Carlo method to confirm the effectiveness of the scattered component inhibiting method of this embodiment shall be explained as follows:

An attempt to simulate with a computer the behavior of a light in a living body tissue is reported by Wilson and Hasegawa. The Monte Carlo method and diffusing formula are used to simulate the behavior of a scattered light. Here, the light propagation in the living body tissue was simulated by the Monte Carlo method to evaluate the effectiveness of present method.

Figure 5:
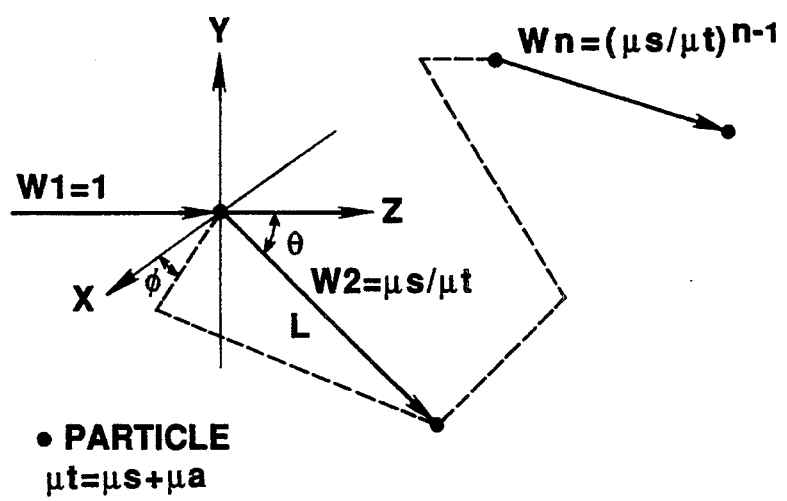
FIG. 5 is an explanatory diagram showing a simulation model of the propagation in a living body tissue of a light particle.

In the Monte Carlo method, the living body tissue is considered to be an aggregation of scattered particles and absorbed particles and the colliding process between the light and particles is calculated as a probability matter. First of all, a light is considered to be a minute light bundle particle. This shall be called here a light particle, though the physical meaning is different. As shown in FIG. 5, the light particle repeats a collision with particles such as tissue cells and red blood cells, and advances in the living body. In every collision, the light is scattered and absorbed. First of all, if the light particle is incident in the z direction and collides with a particle at the origin of the x, y and z axes, the light particle will be scattered in the spherical coordinate system $(\theta, \phi)$ direction and its intensity will be attenuated by a factor of $\mu$ s/($\mu$ s+$\mu$ a). Further, after the collision, the light particle advances for a distance L and again collides with the next particle. Here, $\mu$ s (mm$^{-1}$) represents a scatter coefficient, $\mu$ a (mm$^{-1}$) represents an absorption coefficient. L, $\theta$ and $\phi$ are calculated by the following formulae, respectively, from random numbers $R_1$, $R_2$, and $R_3$:

$$L = \{-\log(R_1)\}/(\mu a + \mu s) \qquad 1$$

$$\theta = f^{-1}(R_2) \qquad 2$$

$$\phi = 2\pi R_3 \qquad 3$$

f ($\theta$) in the formula (2) represents an angular distribution (scattered pattern) of the scattered light intensity by the particle as represented by a function.

It is known that cellular tissues and red blood cells show a strong forward scatter against a visible to near infrared light, but it has been reported that a whole living body tissue is optically thick enough to be able to be treated as producing an equidirectional scatter. The scattered particles of the milk ball suspension used in the experiment are casein particles and their scattering pattern substantially coincides with the equidirectional scatter from the calculation. Here, the simulation was made in the case of the equidirectional scatter of the largest influence of the scatter. f($\theta$) of the equidirectional scatter is represented by the following formula:

$$f(\theta) = (1 - \cos \theta)/2 \qquad 4$$

Figure 6:
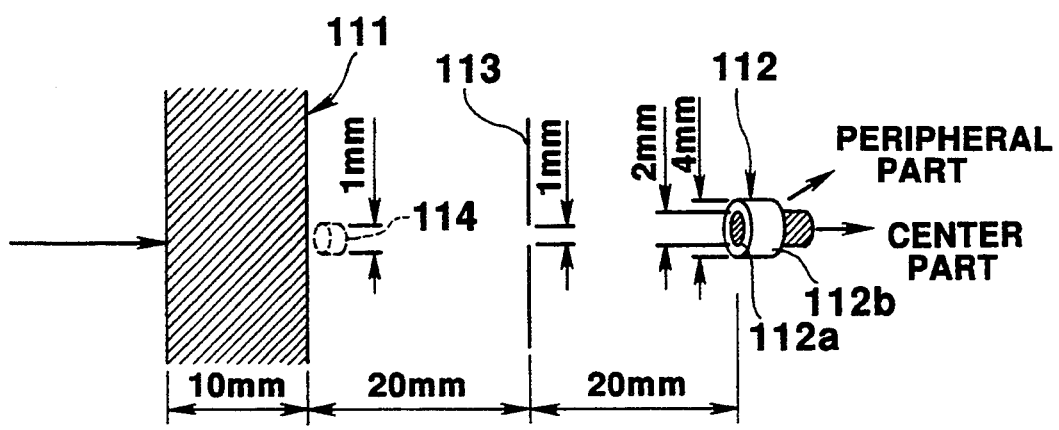
FIG. 6 is an explanatory view showing the arrangement of a detecting system assumed in the simulation.

FIG. 6 shows the following simulation:

First of all, a light particle was made a delta function (a point light source and half value width of zero) in respect of the space and time and was radiated to a sample 111. Here, the thickness of the sample was made 10 mm, the scatter coefficient is of the scattering object was made $\mu$ s=1.5 and the absorption coefficient $\mu$ a was made $\mu$ a=0.0. In the actual living body, the absorption coefficient is not zero but here, in order to see the influence of the scatter, the absorption coefficient was made zero. On the detecting side, a detector 112 of a structure of two concentric layers was arranged in a position separated 40 mm on the extension of the optical axis from the sample 111. This detector 112 was formed of a circular detector (of an outside diameter of 2.0 mm) 112a in the center part and a donut-like detector (of an inside diameter of 2.0 mm and outside diameter of 4.0 mm) 112b in the peripheral part. Further, in order to limit the incident angle, a throttle 113 of an inside diameter of 1.0 mm was arranged in the center of the detector 112 and sample 111. For this arrangement, the motion of the light particle was calculated and the time distributions of the lights reaching the respective detectors 112a and 112b were determined. For comparison, a system where a detector 114 of a diameter of 1 mm was arranged just after the sample 111 was also calculated. Here, the incident pulse is made a delta function but an actual incident pulse has a limited time width and its spatial size is not negligible as compared with the thickness of the example. Therefore, the incident waveform was assumed to be a normal distribution function (of a half value width of 40 ps) and the emitted pulse waveform was determined by a folding integration. The number of the calculated incident light particles was 8 million.

Figure 7A:
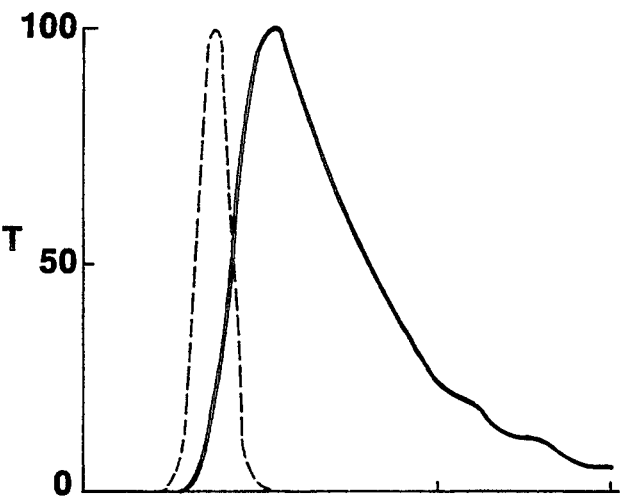
FIGS. 7(A) to (C) are waveform diagrams respectively showing the simulation results.
Figure 7B:
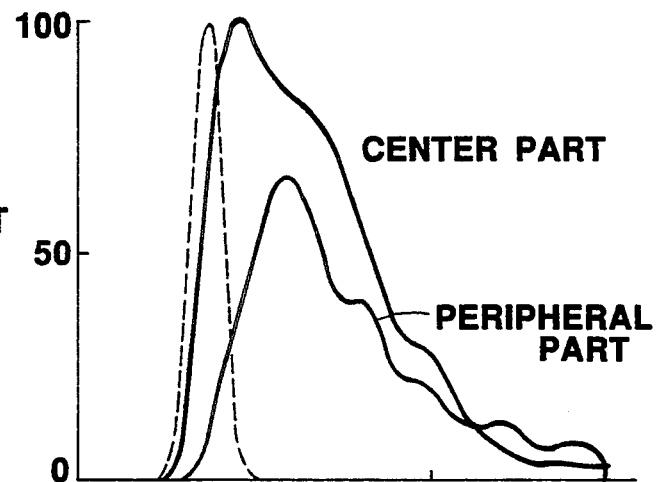
Figure 7C:
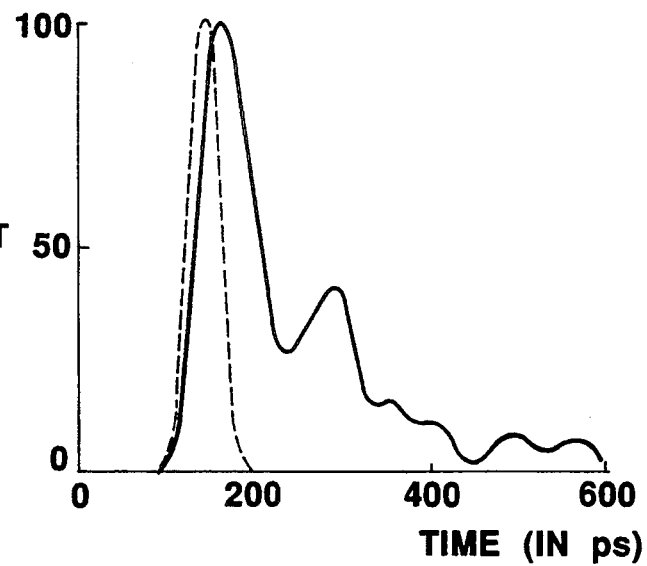

In FIGS. 7(A) to (C) are shown the results of the simulation. In these diagrams, the abscissa represents the time and the ordinate represents the standardized light intensity. In FIG. 7(A), the solid line represents the time distribution of the light reaching the detector 114 arranged just after the sample and is seen to greatly expand in the scattering component as compared with the incident waveform (broken line). In FIG. 7(B), the solid lines represent the time distributions of the light reaching the center part of the detector 112 of the structure of the two concentric layers and of the light reaching the peripheral part. The straight advancing light is included on the optical axis. By passing through the collimation system by the pinhole 113, the scattered component is inhibited to some extent and the straight advancing component of the light reaching the center part increases relatively. Therefore, there is shown a characteristic that, as compared with the waveform in FIG. 7(A), the light intensity rises at an earlier time and the peak is forward. On the other hand, the light reaching the peripheral part is only the scattered light and therefore there is shown a characteristic that the rise of the light intensity is delayed as a whole as compared with the center part and the waveform in FIG. 7(A). Further, FIG. 7(C) is of the result of determining the differences of the light intensity at respective times against the time analyzed waveforms in the center part and peripheral part in FIG. 7(B). Thus, it is understood that the scattered component will be canceled by the difference between the waveforms, the component late in the time will decrease and the waveform will become close to the incident waveform and will have a peak at an early time. That is to say, it is considered that, by detecting the peak of this light, the straight advancing light component can be extracted. Now, it is considered that a large surge is seen in the attenuated part of each time analyzed waveform because the dispersion of the data caused by the shortage of the number of the light particles in the simulation is smoothed by the folding integration with the incident pulse waveform to generate the large surge.

In the above, it is shown that the method of this embodiment in which the space difference and time separation are combined by the computer simulation is effective to inhibit the scattered component and to image at a high space resolution the internal structure of the scattering object.

The space-time scattered component inhibiting system using the method of this embodiment shall be explained in the following with reference to FIGS. 8 to 11.

FIG. 8 shows the summary of said system. This system is provided with an Nd:YAG laser 121 as a light radiating means and a pinhole 123 having the optical axis correctly aligned with the optical axis of the incident beam so as to be opposed to said laser 121 by holding a sample between. The light having passed through this pinhole 123 is led to a streak camera 125 through an optical fiber bundle 124. Said optical fiber bundle 124 consists of a fiber bundle of a structure of two concentric layers at the entrance end and is branched to be Y-like on the exit end sides of the center part 124a and peripheral part 124b. The output of this streak camera 125 is processed by a signal processing apparatus 126 and (personal) computer 127 and the time analyzed waveform of the emitted pulse is observed. A half mirror 128 is provided between the laser 121 and sample 122. The light reflected by this half mirror 128 is received by a photodiode 129 and is made a trigger signal of the streak camera 125.

In this system, a beam-like pulse light is radiated to the sample 122 from the laser 121 and the transmitted and scattered light having passed through the sample 122 are received by the optical fiber bundle 124 through the pinhole 123. The light having entered the center part 124a and peripheral part 124b of this fiber bundle 124 is separated and emitted from the exit end of the optical fiber bundle 124. When the optical axis of the incident beam is arranged as correctly aligned with the center axis of such optical fiber bundle, the sum of the straight advancing component and scattered component of the transmitted light will be detected in the center 124a and only the scattered component will be detected in the peripheral part 124b. Therefore, when they are simultaneously input into the streak camera 124, the obtained time analyzed waveforms are processed by the signal processing apparatus 126 and computer 127 and the difference between the two time analyzed waveforms is determined, the scattered component will be canceled and the straight advancing component will be extracted.

In the experiment, as a collimating system for limiting the scattered light to some extent, the fiber (000A014 of a center part outside diameter of 2.2 mm, peripheral part inside diameter of 3.0 mm and outside diameter of 3.8 mm manufactured by Sumita Optical Glass Co.) was separated by 80 mm from the sample and a pinhole (of a diameter of 1 mm) was arranged intermediately between them. A container made of acrylic, having an inner wall distance of 20 mm, filled with a milk ball suspension (of 15 g/l of defatted powdermilk) and having a knife edge 122a arranged in the central part was used for the sample 122. The spatial resolution of the transmitted image near the knife edge 122a in this sample 122 was measured.

FIGS. 9 and 10 show the results of measuring the time analyzed waveform of the knife edge image by using said system. FIG. 9 shows the time analyzed waveforms as detected in the fiber center part 124a. FIG. 10 shows the results of measuring the difference between the time analyzed waveform detected in the fiber center part 124a and the time analyzed waveform detected in the fiber peripheral part 124b. It is understood that the scattered component is so greatly inhibited in the waveform of the difference result as seen in the waveform in FIG. 9 that the waveform approaches the incident pulse waveform shown on the upper left in each diagram and the spatial resolution of the end periphery of the knife edge 122a is greatly improved.

The results of determining the transmitted image of the knife edge 122a from the thus obtained time analyzed waveform are shown in FIG. 11. In the diagram, C represents the results of detecting the peak of the waveform obtained in the fiber center part 124a and shows that the edge image is greatly smoothed as compared with water (A) having no influence of the scatter. On the other hand, in the results (B) of the difference by the method of this embodiment, the influence of the scatter reduces and the case (A) having no scatter is approached. Here, in (B) and (C), the reduction of the output is locally seen and is considered to be caused by the fluctuation of the laser output or the dirty sample cell surface but not to show the reduction of the spatial resolution.

As in the above, by combining the space difference and time separation, a scattered component inhibiting effect larger than in the case of working item individually has been confirmed.

FIG. 12 shows a schematic formation of a perspective apparatus enabling a perspective view over a wide range.

In this apparatus, a beam of light emitted from a light source 131 is spatially scanned by using, for example, a rotary mirror 132. A detector group 134 consisting of many concavely arranged optical detectors is provided in a position opposed to the rotary mirror 132 by holding a non-transparent space 136 between so that the outputs of the respective optical detectors of this detector group 134 may be input into a signal processing operating apparatus 135. The scanning by the rotary mirror 132 and the processing by the signal processing operating apparatus 135 are synchronized by a synchronizing signal from a synchronizing signal generator 133.

In this apparatus, the beam of light emitted from light source 131 is spatially scanned within the space 136 by using the rotary mirror 132. The sum of the straight advancing component and the scattered component is detected by the detectors opposed to the beam light of said detector group 134 and only the scattered component is detected by the other detectors. In the signal processing operating apparatus 135, by operating to obtain the difference between the detected output of the sum of the straight advancing component and scattered component and the detected output of only the scattered component, the scattered component is inhibited and the object and structure within the space 136 non-transparent due to the light scattering can be made visible. The scattered component can be spatially inhibited by making the emitted light of said light source 131 a continuous light but, by making the emitted light of the light source 131 a pulsed light, by combining the space difference and time separation in the method of this embodiment, the scattered component can be more effectively inhibited.

Thus, according to this embodiment, the scattered component in the light having passed through the examined object can be inhibited and such a strong scattering substance which has so far been considered to be impossible to be viewed perspectively can have a transmitted image high in measured space resolution.

In the spatial method wherein the scattered component is inhibited by the spatial difference between the output of the detector arranged on the optical axis and the output of the detector arranged outside the optical axis by using a continuous light, it has been found that, in the case of a very strong scatter, the straight advancing component will be embedded by the scattered component and the coefficient at the time of the difference will be difficult to determine. If the collimation is made strong, the rate of the straight advancing component will increase and the effect will be improved but, on the other hand, the optical axis will become difficult to adjust. Also, in the time method inhibiting the scattered component by detecting the light having arrived early in the time by using a pulsed light, it has been found that the limited time width of the incident pulse waveform reduces the scattered component inhibiting effect. However, in fact, there is a limit to shortening the pulse width of the incident light and it has been found necessary to deconvolute the output waveform with the input waveform.

In the method of this embodiment in which the space method and time method are combined, these problems are reduced to some extent. Therefore, it has been found advantageous to apply this method to such a sample as a living body tissue in which the amount of scatter is very high, the discontinuity of the refractive index is high and the optical axis is difficult to adjust.

Thus, it has been found that, in the state of a weak scatter, the spatial method which is a simple apparatus and easy to realize is effective and, in the state of a great amount of scatter, the method of this embodiment in which the space difference and time separation are combined is effective.

FIGS. 13 to 20 show the third embodiment of the present invention.

In the scattered component inhibiting method of this embodiment, a light radiated to an examined object is modulated in a period of a fixed time and the light having passed through the examined object is detected in phase to separate the straight advancing component. The scattered component of the light having passed through the examined object has a longer propagating light path than the straight advancing component. Hence, in the case where a modulated light is radiated to the examined object, the phase of the scattered component will be delayed to be later than the phase of the straight advancing component. Therefore, in this embodiment, by using a phase difference detecting apparatus (for example, an interfering system) in which a detecting system of a high sensitivity is easily obtained, a component synchronized in phase is removed, the straight advancing component is extracted and the scattered component is inhibited.

The schematic formation of the apparatus realizing the method of this embodiment shall be explained by using FIG. 13. This apparatus comprises a light source 141, a light modulator 142 modulating the emitted light of this light source 141, a detector 144 detecting the light modulated by this light modulator 142 and having passed through an examined object 143, a synchronous detector 145 extracting a component synchronized in phase with the modulation by the light modulator 142 and a signal processing apparatus 146 processing the output of this synchronous detector 145.

In this apparatus, the emitted light of the light source 141 is modulated by the light modulator 142 and is radiated to the examined object 143. The light having passed through this examined object 143 is detected by the detector 144 and the component synchronized in phase with the modulation by said light modulator 142 of the output of said detector 144 is extracted. A transmitted image, for example, of the examined object 143 is determined by using the component extracted by said synchronous detector 145 in the signal processing apparatus 146.

As shown in FIG. 14, the phase delay by the scatter of the examined object 143 has a distribution having a peak at a phase delay time. In this embodiment, as shown in FIG. 15(A), the incident light for the examined object 143 is modulated with a period twice the phase delay time T corresponding to said peak. That is to say, the phase delay component by the scatter is not superimposed on the straight advancing light component. The sum of such straight advancing component as is shown in FIG. 15(B) and such scattered component as is shown in FIG. 15(C) enters the detector 144. By synchronously detecting the output of this detector 144 on the basis of a signal from the light modulator 142 and extracting a predetermined phase component, the straight advancing component is extracted and the scattered component is inhibited.

Such various kinds of the incident light modulating systems as are shown in FIG. 16 are considered. In FIG. 16, (A) shows a modulating signal representing a period of the modulation, (B) shows an intensity modulation (IM) directly modulating the light intensity, (C) shows a frequency modulation (FM/IM) modulating the frequency of the intensity modulation, (D) shows a phase modulation (PM/IM) modulating the phase of the intensity modulation, (E) shows an amplitude modulation (AM/IM) modulating the amplitude of the intensity modulation and (F) shows a wavelength modulation (WLM) modulating the wavelength itself of the incident light and a modulation making each a pulse is also considered.

In the IM to AM/IM shown in FIG. 16(B) to (E) among these modulating systems, the light passing through the examined object 143 is converted to an electric signal by the detector 144 and is then correlated with the synchronizing signal from the light modulator 142 by the synchronous detector 145 so that phase difference component, that is, the scattered component may be inhibited.

In the case of using the WLM shown in FIG. 16(F), the scattered component inhibiting apparatus is made of such formation as is shown in FIG. 16(F). In this apparatus, a wavelength variable laser 151 (FIG. 17) is used for the light source and the wavelength of the emitted light of this laser 151 is varied by a modulator 152 so that the emitted light of the laser 151 may be modulated in the wavelength. The emitted light of the laser 151 is branched into two lights by a semi-transparent mirror 153 and one light (transmitted light) passes through the examined object 143 and enters a semi-transparent mirror 156. The other light (reflected light) branched by the semi-transparent mirror 153 is reflected by mirrors 154 and 155 and enters the semi-transparent mirror 156. By this semi-transparent mirror 156, the light having passed through the examined object and the reference light having detoured the examined object are mixed to interfere with each other and are correlated with each other and the phase delay component (scattered component) is inhibited. This mixed light is detected by a detector 157. When the output of this detector 157 is detected by using a synchronizing signal from the modulator 152 by a detector 158, a signal having had the phase difference component (scattered component) inhibited will be obtained.

FIG. 18 shows the schematic formation of a scattered component inhibiting apparatus in the case of using a reference light to inhibit the scattered component as in FIG. 17.

In the apparatus shown in this drawing, the emitted light of a laser 161 as a light source is modulated by a light modulator 162 and is branched into two lights by a semi-transparent mirror 163. One branched light (transmitted light) passes through the examined object 143 and enters a phase difference detecting apparatus 165. The other light (reflected light) branched by the semi-transparent mirror 163 is reflected by a mirror 164 and enters the phase difference detecting apparatus 165. In the phase difference detecting apparatus 165, the component synchronized with a predetermined phase in the light passing through the examined object 143 on the basis of the light (reference light) having detoured the examined object 143 is removed so that the straight advancing component may be extracted and the scattered component may be inhibited. When the output of the phase difference detecting apparatus 165 is processed by a signal processing apparatus 166, the transmitted image, for example, of the examined object 143 will be determined.

FIG. 19 shows a concrete formation example of the apparatus of FIG. 18.

In this apparatus, one light (transmitted light) branched by the semi-transparent mirror 163 of the light emitted from the laser 161 and modulated by the light modulator 162 passes through the examined object 143 and enters a semi-transparent mirror 169. The other light (reflected light) branched by the semi-transparent mirror 163 is reflected by the mirrors 164 and 168 and enters the semi-transparent mirror 169. By this semi-transparent mirror 169, the light having passed through the examined object and the reference light having detoured the examined object are mixed to interfere with each other. This mixed light is detected by a detector 157. The output of this detector 157 is input into a heterodyne detector 171 which extracts the straight advancing component and inhibits the scattered component by taking the component synchronized in the phase out of the output of the detector 157 by using the synchronizing signal from an oscillator 167 generating the synchronizing signal for the light modulator 162.

FIG. 20 shows another concrete information example of the apparatus of FIG. 18.

In this apparatus, the light emitted from the laser 161 is branched by a semi-transparent mirror 172. One branched light (transmitted light) is modulated by an acoustic optical device 173, passes through the examined object 143, is reflected by a mirror 174 and enters a semi-transparent mirror 176. The other light (reflected light) branched by said semi-transparent mirror 172 is reflected by a mirror 175 and enters said semi-transparent mirror 176. By this semi-transparent mirror 176, the light having passed through the examined object 143 and the reference light having detoured the examined object are mixed and correlated with each other and the phase delay component (scattered component) is inhibited. This mixed light is detected by the detector 157. The output of this detector 157 is passed through a low-pass filter (LPF) 177 to obtain a signal having had the phase difference component (scattered component) inhibited. The output of this low-pass filter is input into a signal processing apparatus 178.

As explained above, in this embodiment, when a modulated light is radiated to an examined object and the component synchronized with the phase of the straight advancing light of the light having passed through the examined object is removed, the straight advancing component will be extracted and the scattered component will be inhibited so that even such substance of a strong scatterability as has been considered to be unable to be perspectively viewed may be measured as a transmitted image high in spatial resolution.

FIGS. 21 to 36 show the fourth embodiment of the present invention.

In the scattered component inhibiting method of this embodiment, the wavelength of the light radiated to an examined object is varied and the difference in the characteristic between the respective wavelengths is utilized to inhibit the scattered component. That is to say, when the light is radiated to the examined object, as shown in FIG. 31, the scatter coefficient influencing the intensity of the scattered light will not vary greatly with the wavelength inhibit the absorption coefficient influencing the intensity of the straight advancing light will vary greatly with the wavelength. For the light incident upon the examined object, the received light intensity of the light having passed through the examined object decreases due to the scatter and absorption by the examined object but, by determining the variation (difference) of the received light intensity in the case of varying the wavelength of the incident light by the difference in the wavelength characteristic between the scatter coefficient and absorption coefficient, the scattered component can be inhibited. For the wavelength of the incident light, for example, as λ a and λ b in FIG. 31, the scatter coefficient is among a plurality of wave lengths small in the variation of the difference and the absorption coefficient selects a plurality of wavelengths large in the variation of the difference. The wavelength region which is large in the absorption coefficient and through which no light passes is not used.

Also, as shown in FIG. 36, by detecting the size of the variation among wavelengths of the received light intensity of the light having passed through the examined object 193, the examined object 193 can be discriminated, that is, whether veins or organs are present or not or whether it is of a normal tissue or not can be judged and thereby the information within the living body can be imaged.

The schematic formation of the apparatus for realizing the method of this embodiment shall be explained in the following by reference to FIG. 21. This apparatus comprises a light source 191, a wavelength variable apparatus 192 for varying the wavelength of the emitted light of this light source 191, a wavelength selecting apparatus 194 for receiving the light emitted from this wavelength variable apparatus 192 and having passed through the examined object 193, selecting a plurality of wavelengths and detecting the light intensity of each wavelength, a signal processing apparatus 195 for processing the output of this wavelength selecting apparatus 194 and a driver 196 driving the wavelength variable apparatus 192 and transmitting a synchronizing signal to the signal processing apparatus 195.

In this apparatus, the light emitted from the light source 191 is radiated to the examined object 193. The light radiated to the examined object 193 is varied in the wavelength by the wavelength variable apparatus 192. The light having passed through the examined object 193 is received by the wavelength selecting apparatus 194 and the light intensity in a plurality of wavelengths is detected. Then, in the signal processing apparatus 195, a transmitted image, for example, of the examined object 193 is determined by using the light intensity in a plurality of wavelengths detected by the wavelength selecting apparatus 194. By the wavelength variable apparatus 192, the wavelength of the light radiated to the examined object 193 is varied and, by the wavelength selecting apparatus 194 and signal processing apparatus 195, the variation (difference) of the received light intensity with the variation of the wavelength by the wavelength variable apparatus 192 is determined so that the scattered component may be inhibited.

Four examples of the light source 191 and wavelength variable apparatus 192 shall be explained in the following with reference to FIGS. 22 to 26.

FIG. 22 shows the first example in which a dye laser 201 is used for the light source 191 and wavelength variable apparatus 192 and a diffraction grating 202 of this dye laser 201 is driven by a driver 196. In this example, when the diffracting grating 202 is driven by the driver 196, the wavelength of the light emitted from the dye laser 201 will vary. Such a laser which can vary the wavelength as a wavelength variable semiconductor laser, Alexand light laser or free electronic laser may be used instead of the dye laser 201. FIG. 23 shows the second example in which a white light source 203 emitting a white color is used for the light source 191 and a rotary filter 204 is used for the wavelength variable apparatus 192. The rotary filter 204 has a plurality of color filters (band pass filters) 204a to 204d which transmit lights of wavelengths different from each other and one of which is to be selectively arranged on the light path of the emitted light of the light source 203. In this example, when the rotary filter 204 is rotated, the emitted light of the light source 203 will sequentially pass through the color filters 204a to 204d and the wavelength of the light radiated to an examined object 193 will be switched.

FIGS. 24 and 25 show the third example in which a plurality of semiconductor lasers (mentioned as LD's hereinafter) 205a to 205c are provided for the light source 191 and wavelength variable apparatus 192. The respective LD's 205a to 205c emit lights of respectively different wavelengths $\lambda_1$, $\lambda_2$ and $\lambda_3$. The emitted light of the LD 205a is radiated to the examined object 193 through a mirror 206 and semi-transparent mirrors 207 and 208, the emitted light of the LD 205b is radiated to the examined object 193 through the semi-transparent mirror 207 and 208 and the emitted light of the LD 205c is radiated to the examined object 193 through the semi-transparent mirror 208. The respective LD's 205a to 205c are driven respectively by driving signals $D_1$, $D_2$, $D_3$. In this example, when the LD's 205a to 205c are driven at timings different from each other, respectively, by driving signals $D_1$, $D_2$ and $D_3$, as shown in FIGS. 25(A) to (C), the wavelength of the emitted light will be sequentially switched as shown in FIG. 25(D).

FIG. 26 shows the fourth example in which a plurality of lasers 211a to 211c emitting lights of wavelengths different from each other are provided for the light source 191. The emitted light of the laser 211a is radiated to the examined object 193 through a half-transparent mirror 213. The emitted light of the laser 211b is radiated to the examined object 193 through semi-transparent mirrors 214 and 213. The emitted light of the laser 211c is radiated to the examined object 193 through a mirror 215 and the semi-transparent mirrors 214 and 213. A rotary filter 212 for the wavelength variable apparatus 192 is provided between the lasers 211a to 211c and the semi-transparent mirrors 213 and 214 and mirror 215. One hole 212a is provided on this rotary filter 212 so as to be selectively arranged on the light paths of the emitted lights of the lasers 211a to 211c. In this example, when the rotary filter 212 is rotated, the hole 212a will be selectively arranged on the light paths of the emitted lights of the lasers 211a to 211c and the emitted lights of the lasers 211a to 211c will be sequentially radiated to the examined object 193.

Three examples of the wavelength apparatus 194 shall be explained in the following with reference to FIGS. 27 to 30.

Figure 27:
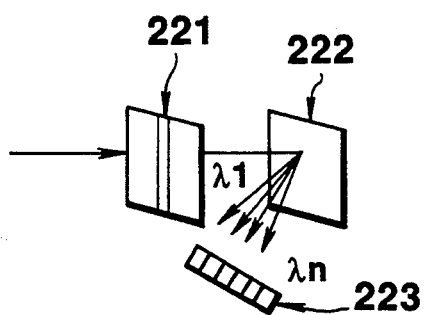
Figure 28:
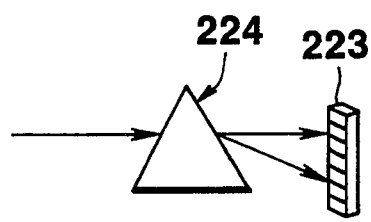

FIG. 27 shows the first example in which a spectroscope comprising a slit 221 arranged on the light path of the light having passed through the examined object, a diffraction grating 222 separating the light having passed through this slit 221 into a plurality of lights of wavelengths $\lambda_1, \ldots \lambda_n$ and an image array 223 having a plurality of light receiving devices for receiving the lights of the respective wavelengths is used for the wavelength selecting apparatus 194. As shown in FIG. 28, a prism 224 be used instead of the slit 221 and diffraction grating 222. Also, a monochrometer may be used instead of the spectroscope shown in FIGS. 27 and 28.

Figure 29:
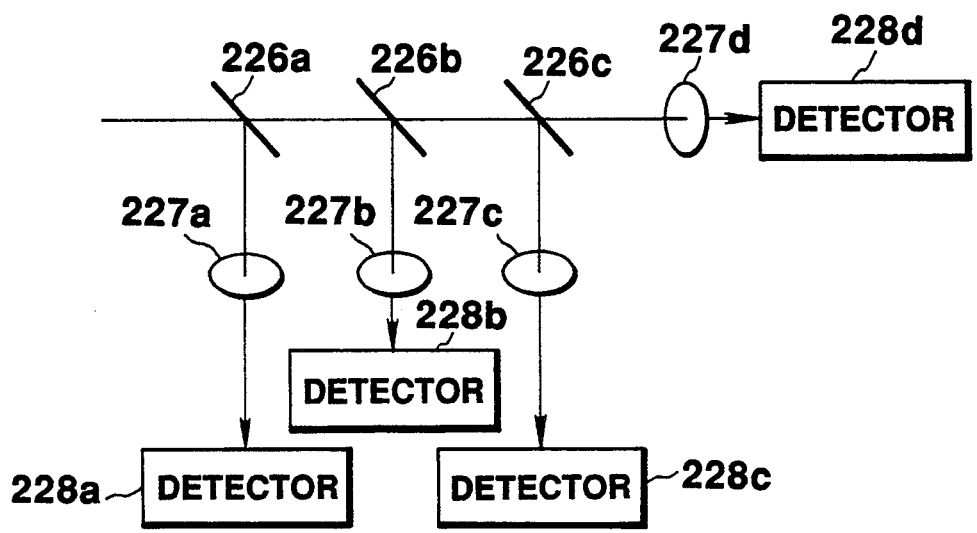

FIG. 29 shows the second example in which the light having passed through the examined object is separated into four light bundles by three beam splitters 226a, 226b and 226c. Color filters 227a to 227d transmitting, respectively, lights of wavelengths different from each other are arranged on the light paths of the respective separated light bundles. The lights of the respective wavelengths having passed through the respective color filters 227a to 7127d are detected, respectively, by detectors 228a to 228d. A dye clock mirror may be used instead of the beam splitters 226a to 226c. In such a case, the color filters 227a to 227d are not required.

Figure 30:
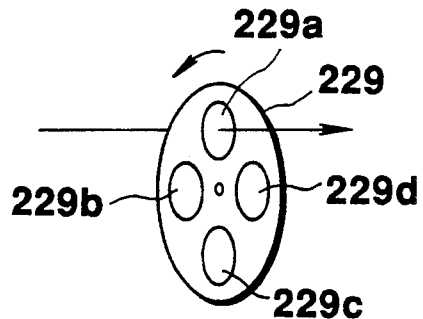

FIG. 30 shows the third example in which a rotary filter 229 is used and has a plurality of color filters 229a to 229d transmitting lights of wavelengths different from each other so that one of these color filters may be selectively arranged on the light path of the light having passed through the examined object. In this example, when the rotary filter 229 is rotated, the light having passed through the examined object will sequentially pass through the color filters 229a to 227d and will be separated into lights of the respective wavelengths. The rotary filter 229 is rotated so as to be synchronized with the timing of switching the wavelength in the wavelength variable apparatus 192.

In this embodiment, as shown, for example, in FIGS. 32(A) to (D), the respective emitting timings of the lights of a plurality of wavelengths $\lambda_1$ to $\lambda_4$ radiated to the examined object from the wavelength variable apparatus 192 are delayed and the emitting period of the light of one wavelength (for example, a period larger than about 10 ns) longer than the passing time made long by the scatter in the examined object 193. Such light passes through the examined object 193 and, in the wavelength selecting apparatus 194, in each of the respective wavelengths $\lambda_1$ to $\lambda_4$, such waveforms as are shown in FIGS. 33(A) to (D) will be detected. When the timings of the waveforms of the respective wavelengths are combined, they will be as shown in FIG. 34. When the rising parts of the waveforms in FIG. 34 are magnified, they will be as shown in FIG. 35. As shown in these diagrams, as the straight advancing part is included in the rising part of the light having passed through the examined object, the intensity will be different depending on the wavelength. On the other hand, as the late part of the light having passed through the examined object is of only the scattered component, the intensity will not vary so much with the variation of the wavelength. In this embodiment, when the differences (such as $\lambda_1 - \lambda_2$ and $\lambda_1 - \lambda_4$) between the intensities of the respective wavelengths particularly in such rising parts of the light having passed through the examined object are determined, more effectively the straight advancing component will be able to be extracted and the scattered component will be able to be inhibited.

As explained above, in this embodiment, when the variation (difference) of the received light intensity of the light having passed through the examined object in a plurality of wavelengths is determined by varying the wavelength of the light radiated to the examined object, the straight advancing component will be extracted and the scattered component will be inhibited. Thereby, even a strongly scattering substance which has been considered to be unable to be perspectively viewed can have a perspective image high in measured spatial resolution.

Here, the experiment and result of obtaining a cross-sectioned image of the examined object shall be explained with reference to FIGS. 37 to 40.

As shown in FIGS. 37 and 38, the living body model for this experiment is provided with a container 251, a rotatable and X-direction movable sample stand 252 and sample 253 fitted to this sample stand 252. Said container 251 is filled with 1.0 g of defatted milk as dissolved per 100 m 1 of water. In this experiment, the transmitted light intensity is measured at intervals of 0.5 mm from the 0-point while scanning the sample stand 252 in the X-direction. The data until 64 mm (127-point) are measured, then the sample stand 252 is rotated by 10 degrees counter-clockwise and the data from 0 to the 127-point are measured in the same manner. This is carried out on the 170-degree part (18 directions) to obtain data of the transmitted light intensity distribution. When these data are re-formed by using an algorithm of X-ray CT, a cross-sectioned image will be obtained. The same experiment is made by using three kinds of light receiving systems. The three kinds of light receiving systems are to arrange a pinhole on the light receiving surface, to use a collimator and to use a collimator and a difference method. Also, for comparison, a collimator was used for the experiment by using water instead of the scattered component.

Among the above mentioned three kinds of light receiving systems, using a collimator and difference method is a spatial method of inhibiting a scattered component by a spatial difference between the output of a detector arranged on the optical axis and the output of a detector arranged outside the optical axis by using a continuous light. This principle shall be explained by using FIG. 39. A laser light emitted from an He—Ne laser 261 passes through such living body model 262 as is shown in FIG. 37 and passes through a collimator 263 correctly aligned with the optical axis of the laser light and a collimator 264 arranged at an angle $\theta$ from said optical axis. The lights having passed through the respective collimators 263 and 264 are received respectively by light receivers 265 and 266. In the light receiver 265, the sum of the straight advancing component and scattered component of the light having passed through the living body model 262 is detected. In the light receiver 266, only the scattered light component is detected. In a differential amplifier 267, by subtracting the value weighting the output of the light receiver 266 from the output of the light receiver 265, the scattered component can be inhibited.

The experimental results are shown in FIG. 40. (A), (B), (C) and (D) show cross-sectioned images obtained as the results of the measurements respectively in the case of using a collimator by using water instead of a scattered body (A), in the case of arranging a pinhole on the light receiving surface (B), in the case of using a collimator (C) and in the case of using a collimator and a difference method (D). It is understood from these views that, in the case of using a collimator and difference method, the scattered component will be best inhibited and a cross-sectioned image high in the spatial resolution will be obtained. The experimenting method explained by using FIGS. 37 and 38 can be also used to confirm the effects of the scattered component inhibiting methods of the other respective embodiments of the present invention.

FIG. 41 shows the fifth embodiment of the present invention.

In this embodiment, the method of timely and spatially inhibiting the scattered component in the second embodiment is applied to the case of detecting the reflected light from the examined object.

In the scattered component inhibiting system of this embodiment, as shown in FIG. 41, an optical fiber bundle 271 of a concentric two-layer structure on the tip side is provided the same as in the optical fiber bundle 124 in the second embodiment. This optical fiber bundle 271 is branched to be Y-like in the central part 271a and peripheral part 271b on the base end side. The peripheral part 271b is connected in the base end part to a time analyzing light measuring apparatus 108. Said central part 271a is connected on the base end surface to an optical fiber bundle 272 on one end surface as opposed to each other so that a predetermined distance may be kept between and the center axes may be aligned with each other. The optical fiber bundle 272 is connected at the other end to the time analyzing light measuring apparatus 108. A beam splitter 283 is arranged between the end surfaces opposed to each other of the central part 271a and optical fiber bundle 272. A throttle 282 having the opening correctly aligned with the center axis of the optical fiber bundle 271 is provided between the optical fiber bundle 271 at the tip and the examined object 281. There are also provided a pulse light source 102 emitting a pulse light and a mirror 284 reflecting the light emitted from this pulse light source 102 and leading it to the beam splitter 283. The light emitted from the pulse light source 102 and reflected by the mirror 284 is reflected by the beam splitter 283 and enters the central part 271a of the optical fiber bundle 271.

The operation of this embodiment shall be explained in the following.

The light emitted from the pulsed light source 102 and reflected by the mirror 284 is reflected by the beam splitter 283, enters the central part 271a of the optical fiber bundle 271, is emitted from the tip of this central part 271a, enters the examined object 281 through the throttle 282 and is partly reflected on the boundary surfaces different in the refractive index within the examined object 281. The reflected light straight advancing light from said boundary surfaces within the examined object on the optical axis of this central part 271a and the scattered light having passed outside the optical axis by scattering enter the central part 271a. The sum of this straight advancing light and scattered light is emitted from the center part 271a at the base end, passes through the beam splitter 283 and is detected in the time analyzing light measuring apparatus 108 through the optical fiber bundle 272. On the other hand, only the scattered light enters the peripheral part 271b of the optical fiber bundle 271 and is detected in the time analyzing light measuring apparatus 108 through the peripheral part 271b.

The same as in the second embodiment, the time analyzing light measuring apparatus 108 detects the time analyzed waveform of the sum of the straight advancing light and scattered light and the time analyzed waveform of only the scattered light and delivers them to a signal process operating apparatus 109 which operates to obtain the difference on the time axis between the two time analyzed waveforms obtained in the time analyzing light measuring apparatus 108 and extracts the straight advancing light.

The other operations and effects are the same as in the second embodiment.

FIGS. 42 and 43 show the sixth embodiment of the present invention.

In this embodiment, the scattered component inhibiting method of the fifth embodiment is applied to an endoscope system for observing an optical cross-sectioned image.

As shown in FIG. 42, the optical cross-sectioned image observing endoscope system comprises an endoscope 301, a light source apparatus 350, video processor 360 and optical cross-section processing apparatus 370 to which this endoscope 301 is connected and a monitor 365 connected to said video processor 360.

The endoscope 301 comprises an elongate flexible insertable part 302, an operating part 303 connected to this insertable part 302 at the rear end and a universal cord 304 extended out of this operating part 303 on the side. Said universal cord 304 is provided at the end with a light source connector 305 removably connected to the light source apparatus 350. A signal cable 306 is extended out of this light source connector 305 and is provided at the end with a signal connector 307 removably connected to the video processor 360, where the operating part 303 is provided with a bending knob 308 for bending a bending part provided in the insertable part 302 and a light guide driving part 310.

The tip part 311 of the insertable part 302 is provided on the side with an observing window 312 and two illuminating windows 313. A light passing cylindrical cover 315 closed at the tip is provided as a measuring window part in the foremost end part said tip part. A channel 316 communicating on the tip side with the interior of said light passing cover 315 and connected on the rear end side to said light guide driving part 310 is provided within said insertable part 302 and operating part 303.

As shown in FIG. 43, an objective lens 318 is provided inside the observing window 312. A CCD 319 is provided in the image forming position of this objective lens 318 and is connected to a driving circuit 320. A signal line 321 connected to this driving circuit 320 is inserted through the insertable part 302, operating part 303, universal cord 304, light source connector 305 and signal cable 306, is connected to the signal connector 307 and is connected to the video processor 360 through this signal connector 307. Said video processor 360 is provided with a video signal processing circuit 361 connected to said driving circuit 320 and a superimposing circuit 362 into which the output signal of this video signal processing circuit 361 is input.

An illuminating light guide 323 on the tip surface is arranged inside said illuminating window 313. This light guide 323 is inserted through the insertable part 302, operating part 303 and universal cord 304 and is connected at the entrance end to the light source connector 305. The light source apparatus 350 to which this light source connector 305 is connected is provided with a lamp 351 and a condenser lens 352 condensing the emitted light of this lamp and making it enter said light guide 323 on the entrance end surface.

An optical cross-sectioned image observing measuring light guide 325, inserted through the channel 316, is of a concentric two-layer structure and has a prism 326 as a reflecting means directing the optical axis sideways of the tip part 311 secured on the tip surface. This prism 326 is arranged within the light passing cover 315. Said light guide 325 is led at the rear end into a light guide driving part 310 to which is connected a light guide 328 at one end. This light guide 328 is connected at the other end to the optical cross-sectioned image processing apparatus 370. On the one end side, the light guide 328 is of a concentric two-layer structure having a central part 328a and peripheral part 328b and, on the other end side, the central part 328a and peripheral part 328b are branched from each other and are respectively connected to an optical cross-sectioned image processing apparatus 370.

Within the light guide driving part 310, a cylindrical mouthpiece 330 is fixed to the light guide 325 at the rear end. Within the light guide driving part 310 is provided a bearing 331 rotatably supporting the mouthpiece 330 and fixed to the light guide 328 at one end. A gear 332 is externally fitted and fixed to the mouthpiece 330 and is meshed with a pinion 333 fixed to the output shaft of a pulse motor 334. This pulse motor 334 and the bearing 331 are fixed to a rack 335 which is meshed with a pinion 337 fixed to the output shaft of a pulse motor 336. Therefore, when the pulse motor 334 is rotated, the light guide 325 will rotate and, when the pulse motor 336 is rotated, the light guides 325 and 328 will advance or retreat.

The optical cross-sectioned image processing apparatus 370 to which the light guide 328 is connected is provided with a streak camera 371 receiving lights from the central part 328a and peripheral part 328b of the light guide 328. This streak camera 371 is connected to a signal processing apparatus 372, which is connected to a computer 373. Also, a beam splitter 374 is provided between the center part 328a of the light guide 328 and the streak camera 371. Within the optical cross-sectioned image processing apparatus 370 are provided a dye laser 375 and Nd:YAG laser 376. The emitted light of the Nd:YAG laser 376 is radiated to a color (for example, Rhodamine G) within the dye laser 375. The emitted light of this dye laser is reflected by the beam splitter 374 and enters the central part 328a of the light guide 328.

The computer 373 forms an optical cross-sectioned image on the basis of data from the signal processing apparatus 372. Its image signal is input into a superimposing circuit 362 within a video processor 360. This superimposing circuit 362 synthesizes the signal from a video signal processing circuit 361 and the signal from the computer 362 so that the endoscope image from the video signal processing circuit 361 and the optical cross-sectioned image from the computer 362 may be displayed in a monitor 365.

The operation of this embodiment shall be explained in the following.

The illuminating light from the light source apparatus 350 is radiated to such examined object as, for example, an internal organ 381 through the light guide 323 and illuminating window 313. The optical image of this internal organ 381 is imaged by the CCD 319. The output signal of this CCD 319 is processed by the video signal processing circuit 361. The video signal from this video signal processing circuit 361 is input into the monitor 365 through the superimposing circuit 362 and the endoscope image is displayed in this monitor 365.

In the case of observing the optical cross-sectioned image of a living body tissue 382 of the organ 381, first of all, a light of several ten pico seconds at a wavelength of 1064 nm is generated from the Nd:YAG laser 376 within the optical cross-sectioned image processing apparatus 370 and is radiated to excite the color within the dye laser 375 so that a light of several pico seconds at a wavelength of 600 to 700 may be generated from this dye laser 375. This light is reflected by the beam splitter 374, enters the central part 328a of the light guide 328, is radiated to the living body tissue of the organ 381 through this central part 328a, the central part of the light guide 325 and the prism 326 and is partly reflected by boundary surfaces different in the refractive index within the living body tissue 382. The straight advancing reflected light and scattered reflected light from said boundary surfaces enter the central part of said light guide 325. The sum of the straight advancing reflected light and scattered reflected light is emitted from the rear end of the central part of the light guide 328 and is detected by the streak camera 371 through the central part 328a of the light guide 328. On the other hand, only the scattered reflected light enters the peripheral part of the light guide 325, is emitted from the rear end of the peripheral part 325 of the light guide 325 and is detected by the streak camera 371 simultaneously with the sum of the straight advancing reflected light and scattered reflected light through the peripheral part 328b of the light guide 328. This streak camera 371 detects the time analyzed waveform of the sum of the straight advancing reflected light and scattered reflected light and the time analyzed waveform of only the scattered reflected light and transmits them to the signal processing apparatus 372 which operates to obtain the difference on the time axis between the two time analyzed waveforms obtained in the streak camera 371, inhibits the scattered reflected light and extracts the straight advancing reflected light.

While scanning the measuring position by advancing, retreating and rotating the light guide 325 with the light guide driving part 310, the above mentioned operation is repeated to obtain data required to form an optical cross-sectioned image of the living body tissue 382. These data are processed by the computer 373 form an optical cross-sectioned image. The endoscope image from the video signal 361 and the optical cross-sectioned image from the computer 362 are synthesized by the superimposing circuit 362 and are displayed in the monitor 365.

Thus, according to this embodiment, not only the ordinary endoscope image but also the optical cross-sectioned image of the living body tissue 382 can be observed.

The other operations and effects are the same as in the fifth embodiment.

FIGS. 44 and 45 show the seventh embodiment of the present invention.

The scattered component inhibiting method of this embodiment is a combination of the method of spatially inhibiting a scattered component as in the first embodiment, and the method of inhibiting a scattered component by utilizing a phase difference in the third embodiment.

As shown in FIG. 44, the scattered component inhibiting system of this embodiment comprises a light source 401, a light modulator 402 modulating the emitted light of this light source 401 and a beam splitter 404 for reflecting the light modulated by this light modulator 402 and radiating the reflected light to an examined object 403. This system further comprises a first collimator 405 correctly aligned with the optical axis of the light from the beam splitter 404 toward the examined light object 403, a light detector 406 detecting the having passed through this collimator 405, a second collimator 407 arranged at a predetermined angle with said optical axis, a light detector 408 detecting the light having passed through this collimator 407, a phase difference detecting apparatus 409 inputting the detected output of the light detector 406 and the modulated signal from the light modulator 402, a phase difference detecting apparatus 410 inputting the detected output of the light detector 408 and the modulated signal from the light modulator 402 and a signal processing apparatus 411 operating by using the respective outputs of the phase difference detecting apparatus 409 and 410.

The operation of this embodiment shall be explained in the following with reference to FIGS. 45(A) to (C).

The light emitted from the light source 401 is modulated by the light modulator 402, is reflected by the beam splitter 404, is radiated to the examined object 403 and is partly reflected by the boundary surfaces different in the refractive index within the examined object 403. The straight advancing reflected light reflected by the boundary surfaces and the scattered reflected light having passed outside the optical axis enter the light detector 406. On the other hand, only the scattered reflected light enters the light detector 408. As shown in FIG. 45(A), the phase difference detecting apparatus 409 determines the relationship between the phase difference of the detected output of the light detector 406 from the modulated signal from the light modulator 402 and the received light intensity to the light detector 406 corresponding to the phase difference. In the same manner, as shown in FIG. 45(B), the phase difference detecting apparatus 410 determines the relationship between the phase difference of the detected output of the light detector 408 from the modulated signal from the light modulator 402 and the received light intensity to the light detector 408 corresponding to the phase difference. The signal processing apparatus 411 operates to subtract the output of the phase difference detecting apparatus 410 weighted as predetermined from the output of the phase difference outputting apparatus 409. Thereby, as shown in FIG.45(C), the intensity distribution of the straight advancing reflected light against the phase difference is determined. The phase difference in FIG. 45(C) corresponds to the depth from the light entering position of the examined object 403.

Thus, according to this embodiment, the straight advancing light component is extracted spatially and by utilizing the phase difference and the scattered light component is inhibited.

As in the third embodiment, the period of the modulation is made larger than the phase delay time by the scatter.

The other operations and effects are the same as in the first or third embodiment.

FIGS. 46 and 47 show the eighth embodiment of the present invention.

In the scattered component inhibiting method of this embodiment, the same as in the fourth embodiment, light having a plurality of wavelengths is radiated to the examined object and the scattered component is inhibited by utilizing the difference of characteristics between the respective wavelengths.

As shown in FIG. 46, the scattered component inhibiting system of this embodiment comprises a YAG-laser 501 and two dye lasers 503 land 505 generating laser lights having different wavelengths. The dye laser 503 generates a light of a wavelength $\lambda_1$. The dye laser 505 generates a light of a wavelength $\lambda_2$. The emitted light of the YAG laser passes through a beam splitter 502 and enters the dye laser 503 and also is reflected by the beam splitter 502, is reflected by a mirror 504 and enters the dye laser 505. The emitted light of the dye laser 503 is reflected by a mirror 506, passes through a beam splitter 507 and is radiated to an examined object 508. The emitted light of the dye laser 505 is reflected by the beam splitter 507 and is radiated to the examined object 508. The light having passed through the examined object 508 is separated in two directions by a beam splitter 509. The light reflected by this beam splitter 509 passes through a filter 510 passing only the light of the wavelength $\lambda_1$, is reflected by mirrors 511 and 512 and enters a streak camera 520. The light having passed through the beam splitter 509 is reflected by a mirror 513, passes through a filter 514 passing only the light of the wavelength $\lambda_2$ and enters the streak camera 520. The output of the streak camera 520 is input into a processing apparatus 521. As in the fourth embodiment, the wavelengths $\lambda_1$ and $\lambda_2$ are selected to be two wavelengths small in the difference of the scatter coefficient of between them and large in the difference the absorption coefficient.

The operation of this embodiment shall be explained in the following with reference to FIGS. 47(A) to (C).

First of all, a light of a wavelength $\lambda_0$ (for example, of 1064 nm) and a half-value width of 40 ps is generated by the YAG laser 501. This emitted light of the YAG laser 501 is divided by the beam splitter 502 in two directions and the divided lights, respectively, enter the two dye lasers 503 and 505 and excite laser lights. Thereby, lights respectively of wavelengths $\lambda_1$ and $\lambda_2$ and a half-value width, for example, of 1 ps will be generated, respectively, from the dye lasers 503 and 505. These two lights are made to again spatially and timely coincide with each other by the mirror 506 and beam splitter 507 and the coincident light enters the examined object 508. The light having passed through the examined object 508 is divided in two directions by the beam splitter 509 and the divided lights pass respectively through the filters 510 and 514 to obtain a light of a wavelength $\lambda_1$ and a light of a wavelength $\lambda_2$. These two lights enter the streak camera 520 so that the light path lengths may be equal. The time analyzed waveforms of the respective lights are determined by this streak camera 520. FIG. 47(A) shows a time analyzed waveform of the wavelength $\lambda_1$. FIG. 47(B) shows a time analyzed waveform of the wavelength $\lambda_2$. The processing apparatus 521 operates to obtain the difference on the time axis between the two time analyzed waveforms obtained in the streak camera 520 so that, as shown in FIG. 47(C), the straight advancing light component of the light having passed through the examined object 508 may be extracted.

The other operations and effects are the same as in the fourth embodiment.

The present invention is not limited to the respective embodiments. A plurality of methods shown in the embodiments may be properly combined. A spatial method or time method may be combined with the method shown in the third or fourth embodiment.

Also, according to the present invention, as the straight advancing component in the light having passed through the examined object is caught, the existing x-ray CT method can be utilized as it is. Not only a perspective in a two-dimensional plane but also a perspective of a cross-sectioned image or three-dimensional cubic structure can be made.

Unlike x-rays and ultrasonic waves, because a light is used for the object interior information sensing means, a perspective image close to the observation with the naked eye can be obtained.

With a perspective by x-rays or ultrasonic waves, it is a main object to obtain object form information but, in the case of using a light, chemical information within the object can be obtained with a spectrochemical knowledge system in the background. For example, a perspective of the energy metabolism distribution within the brain or muscle can be considered.

Because light is used for the object interior information sensing means, the non-contact measurement having little influence of a mechanical vibration or ionization on the examined object can be made.

As explained above, according to the present invention, as the influence of the scatter on the examined object can be inhibited, there is an effect that the examined object interior information can be made visible by using a light at a high resolution.

It is apparent that, in this invention, working modes different in a wide range can be formed on the basis of this invention without deviating from the spirit and scope of the invention. This invention is not restricted by its specific working modes except being limited by the appended claims.

What is claimed is:

1. A method of inhibiting a scattered component in a light having passed through the interior of an examined object, comprising:
    radiating a modulated light to the examined object;
    after passage of said irradiated light through the interior of said examined object, (a) detecting the sum of a straight advancing light component and a scattered light component of said light to give a first detected output, and (b) detecting only said scattered light component of said light to give a second detected output and
    extracting a phase component corresponding to said straight light component of said sum of said light having passed through the interior of said examined object by an operation using said first detected output and said second detected output.

2. A method according to claim 1 wherein said step of detecting the sum includes determining the intensity distribution for the phase difference from said modulated light of only said scattered light component and said extracting step includes operating to obtain the difference between the intensity distribution of only said scattered light component so that the phase component corresponding to said straight advancing light component of said sum may be extracted.

3. A method of inhibiting a scattered component in a light having passed through the interior of an examined object, comprising the steps of:
    radiating to said examined object a light modulated with a period larger than the delay of the propagating time by a scattering in the examined object of the light having passed through said examined object interior;
    detecting a light including a straight advancing light component and a scattered light component, radiated by said radiating step and having passed through the interior of said examined object;
    determining a phase relationship between said radiated modulated light and said detected light;
    extracting said straight advancing light component of the light having passed through the interior of said examined object by extracting a predetermined phase difference component based on said phase relationship of the output detected by said detecting step.

4. A method of inhibiting a scattered component in a light having passed through the interior of an examined object, comprising steps of:
    radiating a light of a plurality of wavelengths to the examined object;
    detecting the light including a straight advancing light component and a scattered light component, radiated by said radiating step and having passed through the interior of said examined object; and inhibiting said scattered light component of the light having passed through the interior of said examined object by an operation using a plurality of detected outputs corresponding to a plurality of said wavelengths detected by said detecting step, wherein said operation is based on how absorption and scattering of said light in said object varies with wavelength.

5. A method according to claim 4 wherein said radiating step includes intermittently radiating said light, said detecting step includes detecting the respective time-analyzed waveforms of the light of the respective wavelengths having passed through the interior of said examined object and said inhibiting step includes operating to obtain the difference between said respective time-analyzed waveforms.

6. An apparatus for inhibiting a scattered component in a light having passed through an examined object interior, comprising:

a radiating means for radiating a light to said examined object, including a means for modulating said light;

a first detecting means for detecting the sum of a straight advancing light component and scattered light component of the light radiated by said radiating means and having passed through the interior of said examined object and providing a first detected output;

a second detecting means for detecting only said scattered light component of the light radiated by said radiating means and having passed through the interior of said examined object, providing a second detected output; and an extracting means for extracting said straight advancing light component of the light having passed through the interior of said examined object by an operation using said first detected output and said second detected output, including a means for extracting the phase component corresponding to said straight advancing light component of said sum.

7. An apparatus according to claim 6 wherein said first detecting means includes a means for determining the intensity distribution for a phase difference from said modulated light of said sum, said second detecting means includes a means for determining the intensity distribution for a phase difference from said modulated light of only said scattered light component and said extracting means includes a means for operating to obtain the difference between the intensity distribution of said sum and the intensity distribution of only said scattered light component so that a phase component corresponding to said straight advancing light component of said sum may be detected.

8. An apparatus for inhibiting a scattered component in a light having passed through the interior of an examined object, comprising:

a radiating means for radiating to said examined object a light modulated with a period larger than the delay of the propagating time by a scattering in said examined object of the light through said examined object interior;

a detecting means for detecting the light including a straight advancing light component and scattered light component, radiated by said radiating means and having passed through the interior of said examined object;

a means for determining a phase relationship between said radiated modulated light and said detected light; and an extracting means for extracting said straight advancing light component of the light having passed through the interior of said examined object by extracting a predetermined phase difference component based on said phase relationship of the output detected by said detecting means.

9. An apparatus for inhibiting a scattered component in a light having passed through an examined object interior, comprising:

a radiating means for radiating a light of a plurality of wavelengths to said examined object;

a detecting means for detecting the light including a straight advancing light component and scattered light component, radiated by said radiating means and having passed through the interior of said examined object; and an operating means for making an operation using a plurality of detected outputs corresponding to a plurality of said wavelengths detected by said detecting means in order to inhibit said scattered light component of the light having passed through the interior of said examined object, wherein said operation is based on how absorption and scattering of said light in said object varies with wavelength.

10. An apparatus according to claim 9 wherein said radiating means intermittently radiates said light, said detecting means includes a means for detecting the respective time-analyzed waveforms of the light of the respective wavelengths having passed through the interior of said examined object and said operating means includes a means for operating to obtain the difference between said respective time-analyzed waveforms.

* * * * *